(12) United States Patent
Wood et al.

(10) Patent No.: US 8,013,162 B2
(45) Date of Patent: Sep. 6, 2011

(54) WATER COMPATIBLE STERICALLY HINDERED ALKOXYAMINES AND HYDROXY SUBSTITUTED ALKOXYAMINES

(75) Inventors: Mervin G. Wood, Mobile, AL (US);
Robert Detlefsen, Putnam Valley, NY (US); James Galbo, Wingdale, NY (US); Wanda Martin, Fruitdale, AL (US); Paul Kondracki, Panaji Goa (IN); Michael P. DiFazio, Mobile, AL (US); Joseph E. Babiarz, Amawalk, NY (US)

(73) Assignee: Ciba Corporation, Tarrytown, NY (US)

( * ) Notice: Subject to any disclaimer, the term of this patent is extended or adjusted under 35 U.S.C. 154(b) by 216 days.

(21) Appl. No.: 12/384,840

(22) Filed: Apr. 9, 2009

(65) Prior Publication Data

US 2009/0202725 A1 Aug. 13, 2009

Related U.S. Application Data

(60) Division of application No. 11/136,792, filed on May 25, 2005, now Pat. No. 7,550,599, which is a continuation-in-part of application No. 10/782,524, filed on Feb. 19, 2004, now abandoned.

(60) Provisional application No. 60/450,262, filed on Feb. 26, 2003.

(51) Int. Cl.
*C07D 401/12* (2006.01)
*C08K 5/3435* (2006.01)

(52) U.S. Cl. ............................ 546/188; 524/99; 546/186
(58) Field of Classification Search .................. 546/188, 546/186; 524/99

See application file for complete search history.

(56) References Cited

U.S. PATENT DOCUMENTS

| | | | |
|---|---|---|---|
| 4,707,507 A | 11/1987 | Akutsu et al. | 524/99 |
| 4,972,009 A | 11/1990 | Suhadolnik et al. | 524/99 |
| 5,004,770 A | 4/1991 | Cortolano et al. | 524/99 |
| 5,096,950 A | 3/1992 | Galbo et al. | 524/99 |
| 5,112,890 A | 5/1992 | Behrens et al. | 524/95 |
| 5,118,736 A | 6/1992 | Ravichandran et al. | 524/100 |
| 5,160,346 A | 11/1992 | Fuso et al. | 4/442 |
| 5,216,156 A | 6/1993 | Galbo et al. | 544/198 |
| 5,286,865 A | 2/1994 | Galbo et al. | 546/188 |
| 6,102,997 A | 8/2000 | Helling et al. | 106/31.43 |
| 6,254,724 B1 | 7/2001 | Seltzer et al. | 162/70 |
| 6,271,377 B1 | 8/2001 | Galbo et al. | 546/14 |
| 6,376,584 B1 | 4/2002 | Galbo et al. | 524/102 |
| 6,392,041 B1 | 5/2002 | Galbo et al. | 544/218 |
| 6,465,645 B1 | 10/2002 | Wood et al. | 544/198 |
| 6,676,735 B2 | 1/2004 | Oki et al. | 106/31.46 |
| 6,719,833 B2 | 4/2004 | Hanmura et al. | 106/31.46 |
| 6,811,597 B2 | 11/2004 | Oki et al. | 106/31.46 |
| 2002/0050226 A1 | 5/2002 | Oki et al. | 106/31.46 |
| 2002/0056534 A1 | 5/2002 | Thomas | 162/72 |
| 2003/0070582 A1 | 4/2003 | Kitamura et al. | 106/31.46 |
| 2004/0011249 A1 | 1/2004 | Oki et al. | 106/31.46 |
| 2004/0074417 A1 | 4/2004 | Biry | 106/31.01 |
| 2005/0272840 A1 | 12/2005 | Pearson et al. | 524/115 |
| 2005/0277713 A1 | 12/2005 | Pearson et al. | 524/99 |
| 2005/0277715 A1 | 12/2005 | Pearson et al. | 524/100 |
| 2005/0277771 A1 | 12/2005 | Pearson et al. | 544/198 |
| 2005/0288400 A1 | 12/2005 | Pearson et al. | 524/86 |

FOREIGN PATENT DOCUMENTS

| | | |
|---|---|---|
| EP | 1174476 | 1/2002 |
| JP | 99170686 | 6/1999 |
| JP | 2000044851 | 2/2000 |
| WO | 01/20078 | 3/2001 |
| WO | 02/100831 | 12/2002 |
| WO | 2004/000809 | 12/2003 |

OTHER PUBLICATIONS

English language abstract for JP 2000044851 (2000).

*Primary Examiner* — Charanjit Aulakh
(74) *Attorney, Agent, or Firm* — Tyler A. Stevenson

(57) ABSTRACT

Sterically hindered hydroxy substituted alkoxyamine stabilizer compounds are made water compatible via certain backbones with affinity towards water. The sterically hindered amines are for example of formulae (5)-(7)

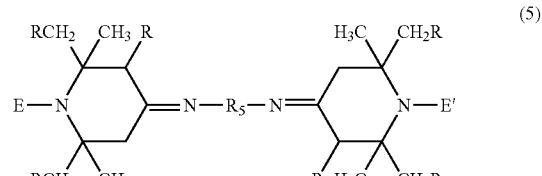

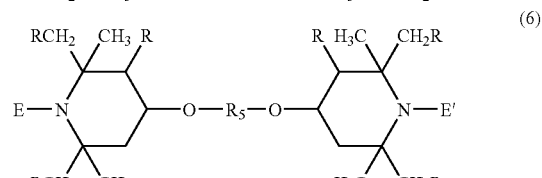

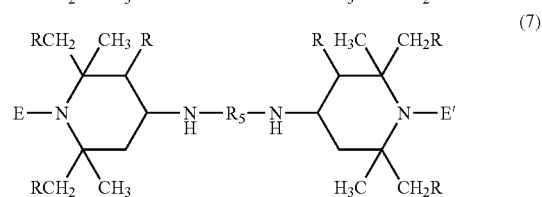

These compounds are particularly effective in stabilizing aqueous polymer systems against the deleterious effects of oxidative, thermal and actinic radiation. The compounds are effective for example in stabilizing water borne coatings, aqueous inks, aqueous ink jet media and photocured aqueous systems.

14 Claims, No Drawings

WATER COMPATIBLE STERICALLY HINDERED ALKOXYAMINES AND HYDROXY SUBSTITUTED ALKOXYAMINES

This application is divisional of U.S. application Ser. No. 11/136,792, filed May 25, 2005, now U.S. Pat. No. 7,550,599, which is a continuation-in-part of U.S. application Ser. No. 10/782,524, filed Feb. 19, 2004, abandoned, which claims the benefit under 35 USC 119(e) of U.S. provisional application No. 60/450,262, filed Feb. 26, 2003, the disclosures of which are incorporated by reference.

The instant invention pertains to sterically hindered alkoxyamine and hydroxy substituted alkoxyamine stabilizer compounds which are water compatible via certain backbones with affinity towards water. These materials are particularly effective in stabilizing aqueous polymer systems against the deleterious effects of oxidative, thermal and actinic radiation. The compounds are effective for example in stabilizing water borne coatings, aqueous inks, aqueous ink jet media and photocured aqueous systems.

U.S. Pat. Nos. 5,004,770 and 5,096,950 describe hindered amine compounds which are substituted on the N-atom by alkoxy moieties herein incorporated by reference.

U.S. Pat. Nos. 6,271,377, 6,392,041 and 6,376,584 disclose sterically hindered hydroxy substituted alkoxyamines herein incorporated by reference.

U.S. Pat. No. 6,254,724 teaches hindered hydroxylamine salt compounds herein incorporated by reference.

U.S. Pat. No. 6,465,645 discloses long chain hindered amine stabilizers herein incorporated by reference.

U.S. Pat. Nos. 5,286,865 and 5,216,156 disclose non-migrating hindered amine stabilizers herein incorporated by reference.

U.S. published app. No. 2002/0050226 and equivalent EP 1174476 disclose certain hindered amines with certain water-soluble groups.

U.S. Pat. No. 6,102,997 discloses certain hindered amine compounds with water solubilizing groups herein incorporated by reference.

JP2000044851 teaches an ink composition that contains certain hindered amine compounds.

JP99170686 teaches hindered amine type additives generically in the ink receiving layer of ink jet recording media.

US 2003/0070582 discloses ink compositions, recording media and an ink jet recording method stabilized with certain hindered amines herein incorporated by reference.

U.S. Pat. No. 6,676,735 disclose aqueous ink compositions stabilized with certain hindered amines herein incorporated by reference.

U.S. Pat. No. 6,811,597 disclose ink compositions, recording media and an ink jet recording method stabilized with certain hindered amines herein incorporated by reference.

US 2004/0011249 discloses ink compositions, recording media, and an ink jet recording method stabilized with certain hindered amines herein incorporated by reference.

U.S. Pat. No. 6,719,833 disclose recording media and an image forming method stabilized with certain hindered amines herein incorporated by reference.

U.S. Pat. Nos. 5,457,204, 5,637,714, 5,665,885, and EP 0,634,399 disclose organic materials stabilized against the damaging influence of light, oxygen, and/or heat by certain hindered amines.

EP 0,413,665 discloses polymer stabilizers containing both hindered amine and nitrone moieties.

U.S. Pat. No. 3,755,586 disclose anti-tussive compositions containing piperidine derivatives.

EP 0,309,402 and EP 0,309,401 disclose certain hindered amines useful for the stabilization of polymer substrates.

JP 09,302,026 discloses certain hindered amines containing polyallylamine polymers.

EP 0,389,419 discloses non-migrating 1-hydrocarbyloxy substituted hindered amines as polymer stabilizers.

EP 0,006,536 disclose piperidine-spiro-hydantoin derivatives and their use as light stabilizers for synthetic polymers.

EP 0,466,647, U.S. Pat. Nos. 5,160,346, and 5,281,707 disclose polyamide compositions stabilized by water-soluble triazine derivatives of hindered amines.

WO 2002/100,831 discloses 4-imino-N-alkoxy piperidine compounds and their use as polymerization regulators.

WO 2004/000,809 discloses cationic alkoxyamines and their use in producing nano particles from natural or synthetic clays.

WO 2001/020,078 disclose cationic nitroxides and hydroxylamine moieties useful for the stabilization of wood pulp and paper.

U.S. Pat. No. 6,102,997 and EP 0,882,600 disclose ink jet systems with improved protection of the ink jet dyes from light.

The present compounds are sterically hindered alkoxyamines and sterically hindered hydroxy substituted alkoxyamines, which are made water compatible or water-soluble with a water compatible or water-soluble backbone.

The instant compounds perform extremely well in aqueous polymeric systems and polar high solids systems. The present compounds exhibit excellent compatibility in polar environments such as polyurethane based coating systems, water borne automotive coating systems, polar recording media and aqueous inks.

DETAILED DISCLOSURE

The present water compatible or water-soluble sterically hindered alkoxyamines and hydroxy substituted alkoxyamines are of the formula (1)-(10)

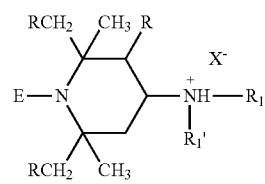

(1)

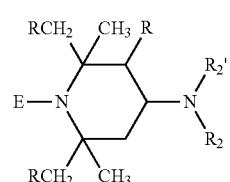

(2)

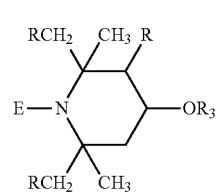

(3)

-continued (4)
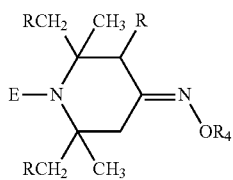

(5)
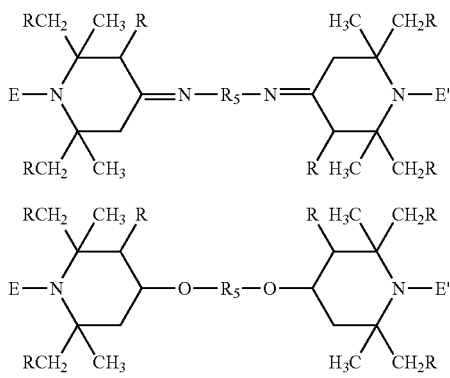

(6)

(7)

(8)
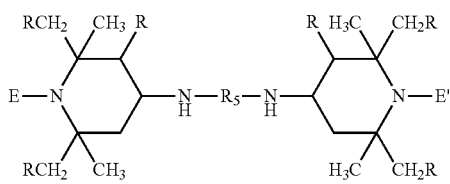

(9)
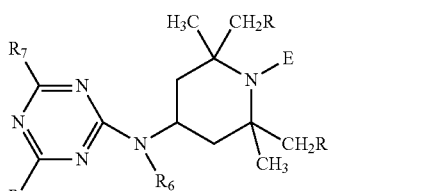

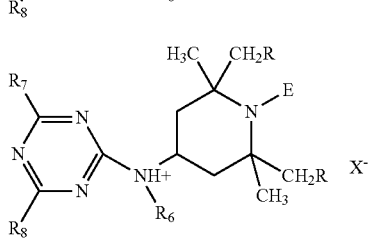

where

E is alkoxy of 1 to 18 carbon atoms, cycloalkoxy of 5 to 12 carbon atoms or aralkoxy of 7 to 15 carbon atoms, or E is —O-T-(OH)$_b$, T is a straight or branched chain alkylene of 1 to 18 carbon atoms, cycloalkylene of 5 to 18 carbon atoms, cycloalkenylene of 5 to 18 carbon atoms, a straight or branched chain alkylene of 1 to 4 carbon atoms substituted by phenyl or by phenyl substituted by one or two alkyl groups of 1 to 4 carbon atoms;

b is 1, 2 or 3 with the proviso that b cannot exceed the number of carbon atoms in T, and when b is 2 or 3, each hydroxyl group is attached to a different carbon atoms of T;

E' is hydrogen, $C_1$-$C_{18}$alkyl, $C_2$-$C_{18}$alkenyl, $C_7$-$C_{15}$-phenylalkyl, $C_2$-$C_{18}$alkanoyl or phenyl, or E' is independently defined as for E, R is hydrogen or methyl, $R_1$ is hydrogen, $C_1$-$C_{12}$alkyl, $C_5$-$C_8$cycloalkyl, $C_5$-$C_8$cycloalkyl substituted by one to three $C_1$-$C_4$alkyl, $C_2$-$C_{12}$alkenyl, phenyl, $C_7$-$C_9$-phenylalkyl, glycidyl, $C_2$-$C_{12}$alkanoyl, $C_6$-$C_9$cycloalkylcarbonyl, $C_2$-$C_{12}$carbamoyl, $C_2$-$C_{12}$alkenoyl, benzoyl, benzoyl substituted by one to three $C_1$-$C_4$alkyl, $C_2$-$C_{12}$alkanoyl substituted by a di($C_1$-$C_6$alkyl) phosphonate, or $R_1$ is $C_2$-$C_{12}$alkyl, $C_2$-$C_{12}$alkanoyl or $C_7$-$C_{18}$phenylalkyl, each interrupted by one to six oxygen, sulfur or —N($R_6$)— groups; $C_1$-$C_{12}$alkyl, $C_2$-$C_{12}$alkanoyl, phenyl or $C_7$-$C_{18}$phenylalkyl, each substituted by one to six hydroxy groups or by one to six —NHR$_6$ groups; $C_2$-$C_{12}$alkyl, $C_2$-$C_{12}$alkanoyl or $C_7$-$C_{18}$-phenylalkyl, each interrupted by one to three —NR$_6$C(O)— groups; or $C_1$-$C_{12}$alkyl, $C_2$-$C_{12}$alkanoyl, phenyl or $C_7$-$C_{18}$phenylalkyl, each substituted by one to three —SO$_3$H groups or by one to three —COOR$_6$ groups; or $R_1$ is said alkyl substituted by a piperazine or by a morpholine group; or $R_1$ is said interrupted group further substituted by one to six hydroxy groups or by one to six —NHR$_6$ groups; or $R_1$ is said interrupted group further substituted by one to three —SO$_3$H groups or by one to three —COOR$_6$ groups;

or $R_1$ is a mono-valent homo- or co-oligomer consisting of monomer units derived from monomers selected from the group consisting of ethylene oxide, propylene oxide, ethylene glycol, propylene glycol, acrylic acid, methacrylic acid, ethylene imine, acrylamide, vinyl formamide, vinyl alcohol and vinyl acetate; which homo- or co-oligomer consists of between 2 and about 24 monomer units;

$R_1$' is independently defined as for $R_1$, $R_5$ is a divalent homo- or co-oligomer consisting of monomer units derived from monomers selected from the group consisting of ethylene oxide, propylene oxide, ethylene glycol, propylene glycol, acrylic acid, methacrylic acid, ethylene imine, acrylamide, vinyl formamide, vinyl alcohol and vinyl acetate; which homo- or co-oligomer consists of between 2 and about 24 monomer units, $R_6$ is hydrogen or $C_1$-$C_6$alkyl, $R_6$' and $R_6$'' are independently defined as for $R_6$, $R_7$ is —N($R_2$)($R_2$') or is chlorine, alkoxy of 1 to 12 carbon atoms, 2-hydroxyethylamino or —N($R_6$)($R_6$');

or $R_7$ is

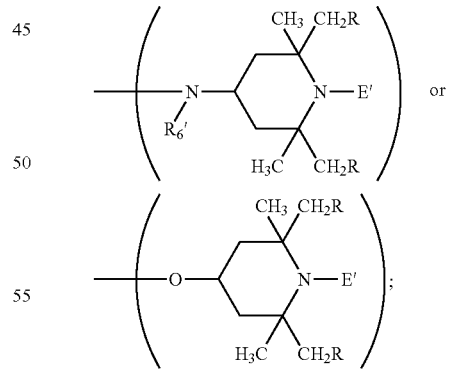

$R_8$ is defined as for $R_7$, where one of $R_7$ and $R_8$ is —N($R_2$)($R_2$');

q is 2 to 8;

X$^-$ is an inorganic or organic anion,

Y$^+$ is a mono-, di- or tri-valent cation, and when E is —O-T-(OH)$_b$, $R_2$ is glycidyl, $C_2$-$C_{12}$alkanoyl substituted by a di($C_1$-$C_6$alkyl)phosphonate, or $R_2$ is $C_2$-$C_{12}$alkyl, $C_2$-$C_{12}$alkanoyl or $C_7$-$C_{18}$phenylalkyl, each interrupted by one to six oxygen, sulfur or —N($R_6$)— groups; $C_1$-$C_{12}$alkyl, $C_2$-$C_{12}$alkanoyl, phenyl or $C_7$-$C_{18}$phenylalkyl, each substituted by one to six hydroxy groups or by one to six —NH$R_6$ groups; $C_2$-$C_{12}$alkyl, $C_2$-$C_{12}$alkanoyl or $C_7$-$C_{18}$phenylalkyl, each interrupted by one to three —N$R_6$C(O)— groups; or $R_2$ is $C_1$-$C_{12}$alkyl, $C_2$-$C_{12}$alkanoyl, phenyl or $C_7$-$C_{18}$phenylalkyl, each substituted by one to three —SO$_3$H groups or by one to three —COO$R_6$ groups; or $R_2$ is said alkyl substituted by a piperazine or by a morpholine group; or $R_2$ is said interrupted group further substituted by one to six hydroxy groups or by one to six —NH$R_6$ groups; or $R_2$ is said interrupted group further substituted by one to three —SO$_3$H groups or by one to three —COO$R_6$ groups; or $R_2$ is $C_1$-$C_{12}$alkyl, $C_2$-$C_{12}$alkanoyl, phenyl or $C_7$-$C_{18}$phenylalkyl, each substituted by one or two —COO$^-$Y$^+$, —N($R_6$)($R_6'$)($R_6''$)$^+$X$^-$ or —SO$_3^-$Y$^+$ groups; or $R_2$ is said $C_1$-$C_{12}$alkyl, $C_2$-$C_{12}$alkanoyl, phenyl or $C_7$-$C_{18}$phenylalkyl, each of which is substituted by one or two —COO$^-$Y$^+$, —N($R_6$)($R_6'$)($R_6''$)$^+$X$^-$ or —SO$_3^-$Y$^+$ groups, each further substituted by one or two —OH, —COO$R_6$ or —NH$R_6$ groups; or $R_2$ is a mono-valent homo- or co-oligomer consisting of monomer units derived from monomers selected from the group consisting of ethylene oxide, propylene oxide, ethylene glycol, propylene glycol, acrylic acid, methacrylic acid, ethylene imine, acrylamide, vinyl formamide, vinyl alcohol and vinyl acetate; which homo- or co-oligomer consists of between 2 and about 24 monomer units, $R_2'$ is defined as for $R_2$ and may also be hydrogen, $R_3$ is defined as for $R_2$ and may also be —SO$_3$H, —PO$_3$H$_2$, —SO$_3^-$Y$^+$ or —PO$_3$H$^-$Y$^+$, and $R_4$ is defined as for $R_2$ and may also be hydrogen, and when E is alkoxy of 1 to 18 carbon atoms, cycloalkoxy of 5 to 12 carbon atoms or aralkoxy of 7 to 15 carbon atoms, $R_2$ is $C_1$-$C_{12}$alkyl, $C_2$-$C_{12}$alkanoyl, phenyl or $C_7$-$C_{18}$phenylalkyl, each substituted by one or two —COO$^-$Y$^+$, —N($R_6$)($R_6'$)$^+$X$^-$ or —SO$_3^-$Y$^+$ groups; or $R_2$ is said $C_1$-$C_{12}$alkyl, $C_2$-$C_{12}$alkanoyl, phenyl or $C_7$-$C_{18}$phenylalkyl, each of which is substituted by one or two —COO$^-$Y$^+$, —N($R_6$)($R_6'$)$^+$X$^-$ or —SO$_3^-$Y$^+$ groups, each further substituted by one or two —OH, —COO$R_6$ or —NH$R_6$ groups, with the proviso that the compound

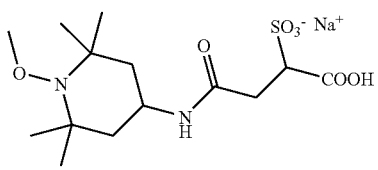

is not included; or $R_2$ is a mono-valent homo- or co-oligomer consisting of monomer units derived from monomers selected from the group consisting of ethylene oxide, propylene oxide, ethylene glycol, propylene glycol, acrylic acid, methacrylic acid, ethylene imine, acrylamide, vinyl formamide, vinyl alcohol and vinyl acetate; which homo- or co-oligomer consists of between 2 and about 24 monomer units;

$R_2'$ is defined as for $R_2$ and may also be hydrogen, $R_3$ is defined as for $R_2$ and may also be —SO$_3$H, —PO$_3$H$_2$, —SO$_3^-$Y$^+$ or —PO$_3$H$^-$Y$^+$, and $R_4$ is defined as for $R_2$ and may also be hydrogen.

For example, E is —O-T(OH)$_b$.

For example, E is 2-hydroxycyclohexyloxy or 2-hydroxy-2-methylpropoxy.

For example, the present compounds are of the formula

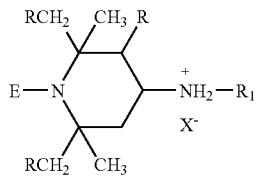

where

E is —O-T(OH)$_b$, $R_1$ is hydrogen, $C_1$-$C_6$alkyl, $C_2$-$C_6$alkanoyl, $C_2$-$C_6$alkyl or $C_2$-$C_6$alkanoyl interrupted by one or two oxygen, sulfur or —N($R_6$)— groups; $C_1$-$C_6$alkyl or $C_2$-$C_6$alkanoyl substituted by one to three hydroxy groups or by one to three —NH$R_6$ groups, $C_2$-$C_6$alkyl or $C_2$-$C_6$alkanoyl interrupted by a —N$R_6$C(O)— group, or is $C_1$-$C_6$alkyl or $C_2$-$C_6$alkanoyl substituted by a —SO$_3$H or by a —COO$R_6$ group, and the other moieties are as previously described.

For example, the present compounds are of the formula

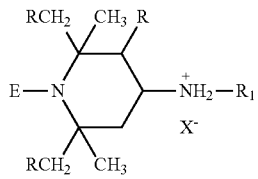

where

E is —O-T(OH)$_b$, $R_1$ is hydrogen, $C_1$-$C_4$alkyl, $C_2$-$C_5$alkanoyl, $C_2$-$C_4$alkyl or $C_2$-$C_5$alkanoyl interrupted by an oxygen, sulfur or —N($R_6$)— group; $C_1$-$C_4$alkyl or $C_2$-$C_5$alkanoyl substituted by an hydroxy group or by a —NH$R_6$ group, $C_2$-$C_4$alkyl or $C_2$-$C_5$alkanoyl interrupted by a —N$R_6$C(O)— group, or is $C_1$-$C_4$alkyl or $C_2$-$C_5$alkanoyl substituted by a —SO$_3$H or by a —COO$R_6$ group, and the other moieties are as described previously.

For instance, the present compounds are of the formula

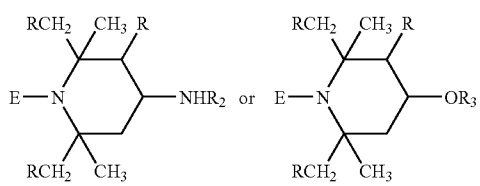

where

E is —O-T(OH)$_b$, $R_2$ and $R_3$ are $C_2$-$C_6$alkyl or $C_2$-$C_6$alkanoyl interrupted by one or two oxygen, sulfur or —N($R_6$)— groups; $C_1$-$C_6$alkyl or $C_2$-$C_6$alkanoyl substituted by one to three hydroxy groups or by one to three —NH$R_6$ groups, $C_2$-$C_6$alkyl or $C_2$-$C_6$alkanoyl interrupted by a —N$R_6$C(O)— group, or $R_2$ is $C_1$-$C_6$alkyl or $C_2$-$C_6$alkanoyl substituted by a —SO$_3$H group or by a —COO$R_6$ group; or $R_2$ and $R_3$ are $C_1$-$C_6$alkyl, $C_2$-$C_6$alkanoyl or $C_7$-$C_9$phenylalkyl, each substituted by a —COO⁻Y⁺, —N($R_6$)($R_6$')⁺X⁻ or —SO$_3$⁻Y⁺ group, and the other moieties are as described previously.

For instance, the present compounds are of the formula where

E is —O-T(OH)$_b$, $R_2$ and $R_3$ are $C_2$-$C_4$alkyl or $C_2$-$C_5$alkanoyl interrupted by an oxygen, sulfur or —N($R_6$)— group; $C_1$-$C_4$alkyl or $C_2$-$C_5$alkanoyl substituted by an hydroxy group or by a —NHR$_6$ group, $C_2$-$C_4$alkyl or $C_2$-$C_5$alkanoyl interrupted by a —NR$_6$C(O)— group, or $R_2$ is $C_1$-$C_4$alkyl or $C_2$-$C_5$alkanoyl substituted by a —SO$_3$H group or by a —COOR$_6$ group; or $R_2$ and $R_3$ are $C_1$-$C_4$alkyl or $C_2$-$C_5$alkanoyl substituted by a —COO⁻Y⁺, —N($R_6$)($R_6$')⁺X⁻ or —SO$_3$⁻Y⁺ group, and the other moieties are as described previously.

For example, the present compounds are of the formula where

E is —O-T(OH)$_b$, $R_4$ is hydrogen, $C_2$-$C_6$alkyl or $C_2$-$C_6$alkanoyl interrupted by one or two oxygen, sulfur or —N($R_6$)— groups; $C_1$-$C_6$alkyl or $C_2$-$C_6$alkanoyl substituted by one to three hydroxy groups or by one to three —NHR$_6$ groups, $C_2$-$C_6$alkyl or $C_2$-$C_6$alkanoyl interrupted by a —NR$_6$C(O)— group, or $R_4$ is $C_1$-$C_6$alkyl or $C_2$-$C_6$alkanoyl substituted by a —SO$_3$H group or by a —COOR$_6$ group; or $R_4$ is $C_1$-$C_6$alkyl, $C_2$-$C_6$alkanoyl or $C_7$-$C_9$phenylalkyl, each substituted by a —COO⁻Y⁺, —N($R_6$)($R_6$')⁺X⁻ or —SO$_3$⁻Y⁺ group, and the other moieties are as described previously.

For example, the present compounds are of the formula where

E is —O-T(OH)$_b$, $R_4$ is hydrogen, $C_2$-$C_4$alkyl or $C_2$-$C_5$alkanoyl interrupted by an oxygen, sulfur or —N($R_6$)— group; $C_1$-$C_4$alkyl or $C_2$-$C_5$alkanoyl substituted by an hydroxy group or by a —NHR$_6$ group, $C_2$-$C_4$alkyl or $C_2$-$C_5$alkanoyl interrupted by a —NR$_6$C(O)— group, or $R_4$ is $C_1$-$C_4$alkyl or $C_2$-$C_5$alkanoyl substituted by a —SO$_3$H group or by a —COOR$_6$ group; or $R_4$ is $C_1$-$C_4$alkyl or $C_2$-$C_5$alkanoyl substituted by a —COO⁻Y⁺, —N($R_6$)($R_6$')⁺X⁻ or —SO$_3$⁻Y⁺ group, and the other moieties are as described previously.

For instance, the present compounds are of the formula where

E is —O-T(OH)$_b$, $R_5$ is polyethylene glycol or polypropylene glycol, and the other moieties are as described previously.

For example, the present compounds are of the formula where

E is —O-T(OH)$_b$, and where $R_x$ is selected from the group consisting of —NH$_2$⁺CH$_2$CH$_2$OH Cl⁻, —NHCH$_2$CH$_2$OH, —NH$_3$⁺⁻OAc, =NOH, —NHCH(CH$_3$)COO⁻K⁺, —NHCH$_2$CH$_2$N(CH$_3$)$_2$⁺⁻OAc, —NHCH$_2$CH$_2$SO$_3$⁻K⁺, —NHCH(COO⁻K⁺)CH$_2$CH$_2$SCH$_3$, —NHCH$_2$COO⁻K⁺, —NHCOCH$_2$OH, —NHCOCH$_2$NHCOCH$_3$, —NHCH$_2$CH$_2$CH$_2$SO$_3$H, —OCH$_2$CH$_2$OH, —OCH(CH$_3$)COO⁻K⁺, —OCH$_2$CH$_2$N(CH$_3$)$_2$⁺⁻OAc, —OCH$_2$CH$_2$SO$_3$⁻K⁺, —OCH(COO⁻K⁺)CH$_2$CH$_2$SCH$_3$, —OCH$_2$COO⁻K⁺, —OCOCH$_2$OH, —OCOCH$_2$NHCOCH$_3$ and —OCH$_2$CH$_2$CH$_2$SO$_3$H; and where $R_y$ is selected from the group consisting of —NHCH$_2$CH$_2$NHCH$_2$CH$_2$NHCH$_2$CH$_2$NH$_2$, —NH$_2$⁺CH$_2$CH$_2$NHCH$_2$CH$_2$NHCH$_2$CH$_2$NH$_2$⁻OAc, —NHPhSO$_3$H, —NHPhSO$_3$⁻K⁺, —NHPhSO$_3$⁻Na⁺, —NH$_2^+$PhSO$_3$H Cl$^-$, —NH(3-carboxy-4-chlorophenyl), —NH(3-COO$^-$Na$^+$-4-chlorophenyl), —NHCH$_2$CH$_2$—(N-piperazine), —NH$_2^+$CH$_2$CH$_2$—(N-piperazine)$^-$OAc and —NH$_2^+$CH$_2$CH$_2$—(N-piperazine)$^-$Cl.

For example, E is alkoxy of 1 to 18 carbon atoms, cycloalkoxy of 5 to 12 carbon atoms or aralkoxy of 7 to 15 carbon atoms.

For instance, E is benzyloxy, methoxy, propoxy, butoxy, pentoxy, hexyloxy, heptyloxy, octyloxy or cyclohexyloxy.

For example, the present compounds are of the formula

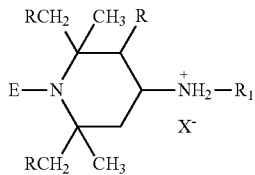

where

E is alkoxy of 1 to 18 carbon atoms, cycloalkoxy of 5 to 12 carbon atoms or aralkoxy of 7 to 15 carbon atoms, R$_1$ is hydrogen, C$_1$-C$_6$alkyl, C$_2$-C$_6$alkanoyl, C$_2$-C$_6$alkyl or C$_2$-C$_6$alkanoyl interrupted by one or two oxygen, sulfur or —N(R$_6$)— groups; C$_1$-C$_6$alkyl or C$_2$-C$_6$alkanoyl substituted by one to three hydroxy groups or by one to three —NHR$_6$ groups, C$_2$-C$_6$alkyl or C$_2$-C$_6$alkanoyl interrupted by a —NR$_6$C(O)— group, or is C$_1$-C$_6$alkyl or C$_2$-C$_6$alkanoyl substituted by a —SO$_3$H or by a —COOR$_6$ group, and the other moieties are as described previously.

For example, the present compounds are of the formula

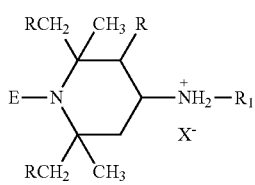

where

E is alkoxy of 1 to 18 carbon atoms, cycloalkoxy of 5 to 12 carbon atoms or aralkoxy of 7 to 15 carbon atoms, R$_1$ is hydrogen, C$_1$-C$_4$alkyl, C$_2$-C$_5$alkanoyl, C$_2$-C$_4$alkyl or C$_2$-C$_5$alkanoyl interrupted by an oxygen, sulfur or —N(R$_6$)— group; C$_1$-C$_4$alkyl or C$_2$-C$_5$alkanoyl substituted by an hydroxy group or by a —NHR$_6$ group, C$_2$-C$_4$alkyl or C$_2$-C$_5$alkanoyl interrupted by a —NR$_6$C(O)— group, or is C$_1$-C$_4$alkyl or C$_2$-C$_5$alkanoyl substituted by a —SO$_3$H or by a —COOR$_6$ group, and the other moieties are as described previously.

For instance, the present compounds are of the formula

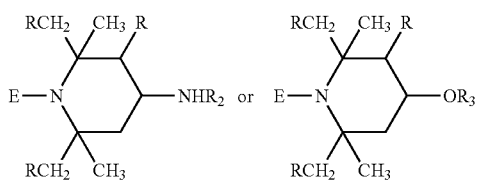

where

E is alkoxy of 1 to 18 carbon atoms, cycloalkoxy of 5 to 12 carbon atoms or aralkoxy of 7 to 15 carbon atoms, R$_2$ and R$_3$ are C$_1$-C$_6$alkyl, C$_2$-C$_6$alkanoyl or C$_7$-C$_9$phenylalkyl, each substituted by a —COO$^-$Y$^+$, —N(R$_6$)(R$_6$')$^+$X$^-$ or —SO$_3^-$Y$^+$ group, and the other moieties are as described previously.

For instance, the present compounds are of the formula

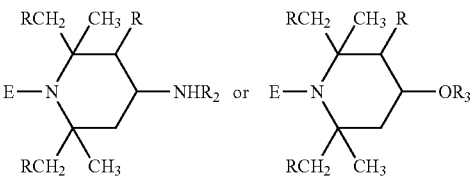

where

E is alkoxy of 1 to 18 carbon atoms, cycloalkoxy of 5 to 12 carbon atoms or aralkoxy of 7 to 15 carbon atoms, R$_2$ and R$_3$ are C$_1$-C$_4$alkyl or C$_2$-C$_5$alkanoyl substituted by a —COO$^-$Y$^+$, —N(R$_6$)(R$_6$')$^+$X$^-$ or —SO$_3^-$Y$^+$ group, and the other moieties are as described previously.

For example, the present compounds are of the formula

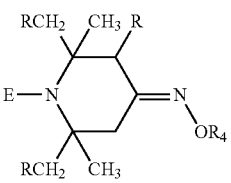

where

E is alkoxy of 1 to 18 carbon atoms, cycloalkoxy of 5 to 12 carbon atoms or aralkoxy of 7 to 15 carbon atoms, R$_4$ is C$_1$-C$_6$alkyl, C$_2$-C$_6$alkanoyl or C$_7$-C$_9$phenylalkyl, each substituted by a —COO$^-$Y$^+$, —N(R$_6$)(R$_6$')$^+$X$^-$ or —SO$_3^-$Y$^+$ group, and the other moieties are as described previously.

For example, the present compounds are of the formula

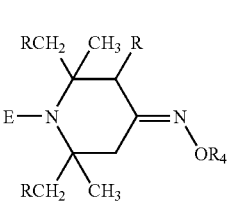

where

E is alkoxy of 1 to 18 carbon atoms, cycloalkoxy of 5 to 12 carbon atoms or aralkoxy of 7 to 15 carbon atoms, R$_4$ is C$_1$-C$_4$alkyl or C$_2$-C$_5$alkanoyl substituted by a —COO$^-$Y$^+$, —N(R$_6$)(R$_6$')$^+$X$^-$ or —SO$_3^-$Y$^+$ group, and the other moieties are as described previously.

For instance, the present compounds are of the formula

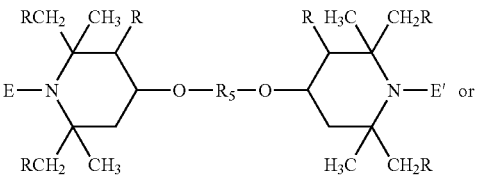

-continued

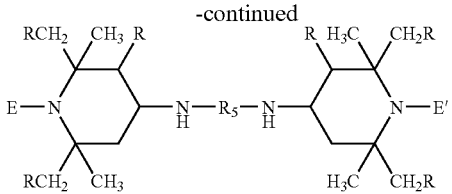

where

E is alkoxy of 1 to 18 carbon atoms, cycloalkoxy of 5 to 12 carbon atoms or aralkoxy of 7 to 15 carbon atoms, $R_5$ is polyethylene glycol or polypropylene glycol, and the other moieties are as described previously.

For example the present compounds are of the formula

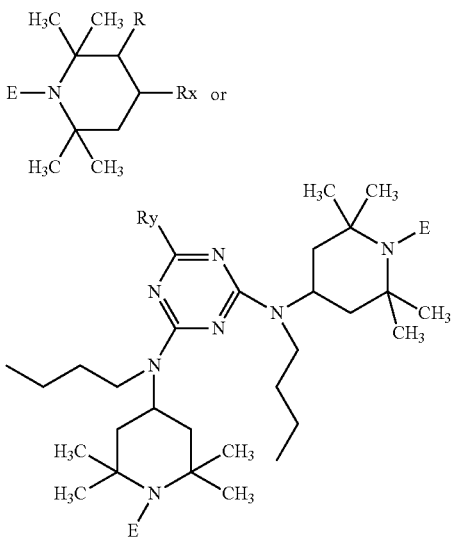

where

E is alkoxy of 1 to 18 carbon atoms, cycloalkoxy of 5 to 12 carbon atoms or aralkoxy of 7 to 15 carbon atoms, and $R_x$ is selected from the group consisting of
—$NH_2^+CH_2CH_2OH$ $Cl^-$, —$NH_3^{+-}OAc$, =NOH, —$NHCH(CH_3)COO^-K^+$, —$NHCH_2CH_2N(CH_3)_2^{+-}OAc$, —$NHCH_2CH_2SO_3^-K^+$, —$NHCH(COO^-K^+)CH_2CH_2SCH_3$, —$NHCH_2COO^-K^+$, —$OCH(CH_3)COO^-K^+$, —$OCH_2CH_2N(CH_3)_2^{+-}OAc$, —$OCH_2CH_2SO_3^-K^+$, —$OCH(COO^-K^+)CH_2CH_2SCH_3$ and —$OCH_2COO^-K^+$ and where $R_y$ is selected from the group consisting of
—$NHCH_2CH_2NHCH_2CH_2NHCH_2CH_2NH_2$, —$NH_2^+CH_2CH_2NHCH_2CH_2NHCH_2CH_2NH_2^-OAc$,
—$NHPhSO_3H$, —NH $PhSO_3^-K^+$, —$NHPhSO_3^-Na^+$, —$NH_2^+PhSO_3H$ $Cl^-$, —NH(3-carboxy-4-chlorophenyl), —NH(3-COO$^-$Na$^+$-4-chlorophenyl), —$NHCH_2CH_2$—(N-piperazine), —$NH_2^+CH_2CH_2$—(N-piperazine)$^-$OAc and —$NH_2^+CH_2CH_2$—(N-piperazine)$^-$Cl.

The solubility of the present sterically hindered amines in water at 20° C. and standard pressure is for example greater than or equal to 1 g/L, for example $\geq$2 g/L, $\geq$5 g/L, $\geq$10 g/L, $\geq$20 g/L, $\geq$30 g/L, $\geq$40 g/L, $\geq$50 g/L, $\geq$60 g/L, $\geq$70 g/L, $\geq$80 g/L, $\geq$90 g/L or $\geq$100 g/L.

Alkyl having up to 12 carbon atoms is branched or unbranched, and is for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl and dodecyl, 1,1,3,3,5,5-hexamethylhexyl.

Alkenyl is an unsaturated version of alkyl, and is branched or unbranched, for example isopropenyl, propenyl, hexenyl, heptenyl, and the like.

Unsubstituted or $C_1$-$C_4$alkyl-substituted $C_5$-$C_8$cycloalkyl is, for example, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. For example cyclohexyl and tert-butylcyclohexyl.

$C_1$-$C_4$Alkyl-substituted phenyl, which contains for example 1 to 3, for instance 1 or 2, alkyl groups, is, for example, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

Phenylalkyl includes substituted phenylalkyl, for example phenylalkyl substituted on the phenyl ring by from 1 to 3 $C_1$-$C_4$alkyl groups or from 1 to 3 halogen or by a mixture thereof, and is for example, benzyl, 4-chlorobenzyl, α-methylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tert-butylbenzyl.

Phenyl includes unsubstituted phenyl and phenyl substituted by from 1 to 3 $C_1$-$C_4$ alkyl groups or from 1 to 3 halogen or by a mixture thereof.

Alkanoyl having up to 12 carbon atoms is branched or unbranched, and is for example formyl, acetyl, propionyl, butanoyl, pentanoyl, hexanoyl, heptanoyl, octanoyl, nonanoyl, decanoyl, undecanoyl or dodecanoyl.

$C_6$-$C_9$Cycloalkylcarbonyl is, for example, cyclopentylcarbonyl, cyclohexylcarbonyl, cycloheptylcarbonyl or cyclooctylcarbonyl.

Carbamoyl of up to 12 carbon atoms is branched or unbranched, and is for example the carbamoyl equivalent of the alkanoyl groups, for example butamoyl, pentamoyl, hexamoyl and the like.

Alkenoyl of up to 12 carbon atoms is branched or unbranched, and is an unsaturated version of alkanoyl.

Benzoyl substituted by one to three $C_1$-$C_4$alkyl, is for example o-, m- or p-methylbenzoyl, 2,3-dimethylbenzoyl, 2,4-dimethylbenzoyl, 2,5-dimethylbenzoyl, 2,6-dimethylbenzoyl, 3,4-dimethylbenzoyl, 3,5-dimethylbenzoyl, 2-methyl-6-ethylbenzoyl, 4-tert-butylbenzoyl, 2-ethylbenzoyl, 2,4,6-trimethylbenzoyl, 2,6-dimethyl-4-tert-butylbenzoyl or 3,5-di-tert-butylbenzoyl.

$C_2$-$C_{25}$Alkanoyl substituted by a di($C_1$-$C_6$alkyl)phosphonate group is, for example, $(CH_3CH_2O)_2POCH_2CO$—, $(CH_3O)_2POCH_2CO$—, $(CH_3CH_2CH_2CH_2O)_2POCH_2CO$—, $(CH_3CH_2O)_2POCH_2CH_2CO$—, $(CH_3O)_2POCH_2CH_2CO$—, $(CH_3CH_2CH_2CH_2O)_2POCH_2CH_2CO$—, $(CH_3CH_2O)_2PO(CH_2)_4CO$—, $(CH_3CH_2O)_2PO(CH_2)_8CO$— or $(CH_3CH_2O)_2PO(CH_2)_{17}CO$—.

$C_2$-$C_{12}$Alkyl interrupted by oxygen, sulfur or by —$N(R_6)$— is, for example, $CH_3$—O—$CH_2$—, $CH_3$—S—$CH_2$—, $CH_3$—$N(CH_3)$—$CH_2$—, $CH_3$—O—$CH_2CH_2$—O—$CH_2$—, $CH_3$—(O—$CH_2CH_2$—)$_2$O—$CH_2$—, $CH_3$—(O—$CH_2CH_2$—)$_3$O—$CH_2$— or $CH_3$—(O—$CH_2CH_2$—)$_4$O—$CH_2$—.

$C_3$-$C_{12}$Alkanoyl interrupted by oxygen, sulfur or by —$N(R_6)$— is, for example, $CH_3$—O—$CH_2CO$—, $CH_3$—S—$CH_2CO$—, $CH_3$—$N(CH_3)$—$CH_2CO$—, $CH_3$—O—$CH_2CH_2$—O—$CH_2CO$—, $CH_3$—(O—$CH_2CH_2$—)$_2$O—

CH$_2$CO—, CH$_3$—(O—CH$_2$CH$_2$—)$_3$O—CH$_2$CO— or CH$_3$—(O—CH$_2$CH$_2$—)$_4$O—CH$_2$CO—.

Substitution by one to six also means of course by 1, 2, 3, 4, 5 or 6 groups, if the length of the chain so allows. Substitution by one to three means of course by 1, 2 or 3 groups, if the length of the chain allows.

Interruption by one to six groups means of course by 1, 2, 3, 4, 5 or 6 groups, if length of the chain allows.

C$_7$-C$_{18}$Phenylalkyl interrupted by oxygen, sulfur or by —N(R$_6$)— and unsubstituted or substituted on the phenyl radical by from one to three C$_1$-C$_4$alkyl groups is branched or unbranched, and is for example phenoxymethyl, 2-methyl-phenoxymethyl, 3-methyl-phenoxymethyl, 4-methyl-phenoxymethyl, 2,4-dimethyl-phenoxymethyl, 2,3-dimethyl-phenoxymethyl, phenylthiomethyl, N-methyl-N-phenyl-aminomethyl, N-ethyl-N-phenyl-aminomethyl, 4-tert-butyl-phenoxymethyl, 4-tert-butyl-phenoxyethoxy-methyl, 2,4-di-tert-butyl-phenoxymethyl, 2,4-di-tert-butyl-phenoxyethoxymethyl, phenoxyethoxyethoxyethoxymethyl, benzyloxymethyl, benzyloxyethoxymethyl, N-benzyl-N-ethyl-aminomethyl or N-benzyl-N-isopropyl-aminomethyl.

The oligomers and co-oligomers of ethylene oxide, propylene oxide, ethylene glycol, propylene glycol, acrylic acid, methacrylic acid, ethylene imine, vinyl alcohol and vinyl acetate are of course oligomeric and co-oligomeric versions of poly(ethylene oxide), poly(propylene oxide), polyethylene glycol, polypropylene glycol, polyacrylic acid, polymethacrylic acid, poly(ethylene imine), polyacrylamide, polyvinylformamide, polyvinyl alcohol and polyvinyl acetate. Oligomers of the above, when mono-valent, may be capped with for example a methyl group or an acetate group, for example the oligomers of polyethylene glycol and polypropylene glycol. Homo- or co-oligomers between 2 and about 24 monomer units are for example between 2 and 20 monomer units, between 2 and 17 monomer units, between 2 and 14 monomer units, between 2 and 11 monomer units, between 2 and 9 monomer units, between 2 and 8 monomer units, between 2 and 6 monomer units, between 2 and 5 monomer units, or between 2 and 4 monomer units. The total number of carbon atoms in the oligomers and co-oligomers is for example less than 20.

X$^-$ is an inorganic or organic anion, such as phosphate, phosphonate, carbonate, bicarbonate, nitrate, chloride, bromide, bisulfite, sulfite, bisulfate, sulfate, borate, formate, acetate (OAc), benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate. Of course, where it is for example a di-, tri- or quaternary valent anion, it forms ion pairs with 2, 3 or 4 cations respectively.

Y$^+$ is a mono-, di- or tri-valent cation and is for example an alkali metal cation, alkaline earth metal cation or aluminum cation. For example, Y$^+$ is Na$^+$, K$^+$, Mg$^{++}$, Ca$^{++}$ or Al$^{+++}$. Of course, where it is a di- or tri-cation, it forms ion pairs with 2 or 3 anions respectively.

Also subject of the present invention are stabilized compositions comprising an organic material subject to the deleterious effects of light, heat and oxygen, and an effective stabilizing amount of a present water compatible or water soluble sterically hindered alkoxyamine or hydroxy substituted alkoxyamine compound.

Another embodiment of the instant invention is a method for stabilizing ink-jet prints, which comprises applying to a recording material for ink-jet printing an ink composition containing a water soluble dye or a solution of a dye in an organic solvent and at least one compound of the formulae (1)-(10) as defined above and drying said recording material.

Another embodiment of the instant invention is a method for stabilizing ink-jet prints, which comprises applying to a recording material for ink-jet printing a casting or coating dispersion or an aqueous or organic solution containing at least one compound of the formulae (1)-(10) as defined above and further applying either an ink composition containing a water soluble dye or a solution of a dye in an organic solvent; or an ink composition containing a water soluble dye or a solution of a dye in an organic solvent and at least one compound of the formulae (1)-(10) and drying said recording material.

The present water compatible or water soluble sterically hindered alkoxyamines or hydroxy substituted alkoxyamine compounds are particularly effective towards preventing color fading of compositions comprising pigments or dyes.

Accordingly, colored compositions comprising pigments or dyes are stabilized compositions according to this invention. That is, the stabilized organic material is the pigment or dye.

The colored compositions are for example compositions comprising dyes, which compositions are selected from the group consisting of ink jet inks, ink jet recording media, coatings, body care products, household products, textiles and fabrics.

The body care products, household products, textiles and fabrics are as described in U.S. application No. 60/377,381, filed May 2, 2002, published as WO 03/103622, the disclosure of which is hereby incorporated by reference.

The body care products are for example hair care products such as shampoos or hair dyeing agents or dentrifices such as mouthwashes.

The present stabilized compositions are for example automotive coating compositions. Compositions to be stabilized including automotive coating compositions are disclosed for example in U.S. Pat. Nos. 5,977,219 and 6,166,218, the disclosures of which are hereby incorporated by reference.

The acrylic resin lacquers which can be stabilized against light, moisture and oxygen in accordance to the instant invention are for example acrylic resin stoving lacquers or thermosetting resins including acrylic/melamine systems which are described, for example, in H. Kittel's "Lehrbuch and Beschichtungen", Vol. 1, Part 2 on pages 735 and 742 (Berlin 1972), "Lackkunstharze" (1977) by H. Wagner and H. F. Sarx on pages 229-238, and in S. Paul's "Surface Coatings: Science and Technology", (1985).

The polyester lacquers which can be stabilized against the action of light and moisture are for instance stoving lacquers described e.g. in H. Wagner and H. F. Sarx, op. cit., on pages 86-99.

The alkyd resin lacquers which can be stabilized against the action of light and moisture in accordance with the instant invention are for example stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99-123). Other crosslinking agents include glycoluril resins, blocked or unblocked isocyanates or epoxy resins. Other lacquers which can be stabilized include those with crosslinkable functionalities such as carbamate and siloxane.

The lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

In addition to acid-catalyzed baked finishes, it is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like. Correspondingly, the epoxide may be utilized as the crosslinking agent for various acrylic or polyester resin systems that have been modified by the presence of reactive groups on the backbone structure.

When used in two-coat finishes, the compounds of the instant invention can be incorporated in the clear coat or both in the clear coat and in the pigmented base coat.

To attain maximum light stability, the concurrent use of other conventional light stabilizers can be advantageous. Examples are UV (ultraviolet light) absorbers of the benzophenone, 2H-benzotriazole, acrylic acid derivatives, oxalanilide, aryl-s-triazine or metal-containing types (e.g. organic nickel compounds). In two-coat systems, these additional light stabilizers can be added to the clear coat and/or the pigmented base coat.

When water soluble, water miscible or water dispersible coatings are desired ammonium salts of acid groups present in the resin are formed. Powder coating compositions can be prepared by reacting glycidyl methacrylate with selected alcohol components.

The instant compounds are also useful in the stabilization of acid catalyzed thermoset resins which are disclosed in U.S. Pat. No. 5,112,890, the relevant parts of which are incorporated herein by reference.

These resins are used in baked enamels or stoving lacquers. Hindered amine light stabilizers are well known to be effective in stabilizing a host of organic substrates including polymers from the deleterious effects of oxygen and light. Such hindered amine light stabilizers have been used in the stabilization of hot-crosslinkable alkyd or acrylic metallic stoving lacquers (see U.S. Pat. No. 4,426,472) and in stabilizing acid-catalyzed stoving lacquers based on hot-crosslinkable acrylic polyester or alkyl resins (see U.S. Pat. Nos. 4,344,876 and 4,426,471). None of the hindered amine light stabilizers of these patents possess the present water-solubilizing structures. The instant compounds have such substitution.

In their industrial uses, enamels with high solids content based on crosslinkable acrylic, polyester, urethane or alkyd resins are cured with an additional acid catalyst. The present water compatible or water soluble sterically hindered alkoxyamines and hydroxy substituted alkoxyamines are suitable in such systems.

The acid catalyzed thermoset enamels must be stabilized in order to function acceptably in end-use applications. The stabilizers are needed to impart greater retention of durability to the cured enamels (as measured by 20° gloss, distinction of image, cracking or chalking); the stabilizers must not retard cure (normal bake for auto finishes at 121° C.; and low bake repair at 82° C.) as measured by hardness, adhesion, solvent resistance and humidity resistance; the enamel should not yellow on curing and further color change on exposure to light should be minimized.

The instant hindered amine light stabilizers fulfill each of these requirements and provide alone or in combination with a UV absorber outstanding light stabilization protection to the cured acid catalyzed thermoset enamels.

The instant invention also pertains to resin systems capable of being fully cured under ambient conditions. For example, applicable resins include alkyd, acrylic, polyester and epoxide resins as described in S. Paul's "Surface Coatings: Science and Technology" (1985), pages 70-310. Various acrylic and modified acrylic resins are described in H. Kittel's "Lehrbuch der Lacke unde Beschichtungen", Vol. 1, Part 2, on pages 735 and 742 (Berlin 1972), and in "Lack-kunstharze" (1977) by H. Wagner and H. F. Sarx, op. cit, on pages 229-238. Typical crosslinkable polyester resins which can be stabilized against the action of light and moisture are described e.g. in H. Wagner and H. F. Sarx, op. cit., on pages 86-99. The unmodified and modified alkyd resins which can be stabilized are conventional resins which are used in trade sales, maintenance and automotive refinish coatings. For example, such coatings are based on alkyd resins, alkyd/acrylic resins and alkyd/silicon reins (see H. Wagner and H. F. Sarx, op. cit., pages 99-123) optionally crosslinked by isocyanates or epoxy resins.

In addition various acrylic lacquer coating compositions are disclosed in U.S. Pat. No. 4,162,249. Other acrylic/alkyd resins with polyisocyanate additives are disclosed in U.S. Pat. No. 4,471,083; and acrylic resins containing either pendant amino ester groups or glycidyl groups are described in U.S. Pat. No. 4,525,521.

The ambient cured coatings stabilized by the instant compounds are suitable both for metal finish coatings and solid shade finishes, especially in the case of retouching finishes. The lacquers stabilized by the instant compounds are preferably applied in a conventional manner by two methods, either by the single-coat method or by the two-coat method. In the latter method, the pigment-containing base coat is applied first and a covering coat of clear lacquer applied over it. When used in two-coat finishes, the instant hindered amine compound can be incorporated in the clear coat or both in the clear coat and in the pigmented base coat.

The instant invention also pertains to abrasion-resistant coating compositions suitable for coating over polycarbonates. Such coatings as described in U.S. Pat. No. 5,214,085 comprise a silyl acrylate, aqueous colloidal silica, a photoinitiator and optionally a polyfunctional acrylate as well as UV absorbers. Such coatings provide resistance after prolonged outdoor exposure to sunlight, moisture, thermal cycling causing yellowing, delamination and formation of microcracks and decreasing transparency.

Related hindered amine stabilizers have been utilized individually and in combination with UV absorbers to improve the performance characteristics of ambient cured coating systems. Notwithstanding such improvements, there still exists a need to further retard the photooxidation and photodegradation of such ambient cured systems and thereby provide increased effectiveness by maintaining the physical integrity of the coatings. Such effectiveness can be manifested by prevention of embrittlement, cracking, corrosion, erosion, loss of gloss, chalking and yellowing of the coating.

It has now been determined that the aforementioned improvements can be achieved by the utilization of the present sterically hindered amines in ambient cured coating systems as is taught in U.S. Pat. No. 5,124,378, the relevant parts of which are incorporated herein by reference. In particular, the physical integrity of the coatings is maintained to a higher degree with significant reduction in loss of gloss and in yellowing. Accordingly, the instant invention relates to the use of the present sterically hindered alkoxyamines and hydroxy substituted alkoxyamines, optionally together with further stabilizers, for stabilizing ambient cured coatings based on alkyd resins; thermoset acrylic resins; acrylic alkyds; acrylic alkyd or polyester resins optionally modified with silicon, isocyanates, isocyanurates, ketimines or oxazolidines; and epoxide resins crosslinked with carboxylic acids, anhydrides, polyamines or mercaptans; and acrylic and polyester resin systems modified with reactive groups in the backbone thereof and crosslinked with epoxides; against the degradative effects of light, moisture and oxygen.

The instant invention also relates to electrodeposited coatings applied to metal substrates where various top coats may be applied thereover. The inclusion of the instant compounds in the E-coat provides delamination resistance to said E-coats. The primary resins in said E-coats are acrylic or epoxy resins. These E-coats are described in European patent application EP 0 576 943 A1.

The instant invention also pertains to water borne architectural coatings, for example, water borne latex emulsion paints.

The instant invention also pertains to ultraviolet light cured (UV cured) coating systems using unsaturated acrylic resins, polyurethane acrylates, epoxy acrylates, polyester acrylates, unsaturated polyester/styrene resins and silyl acrylates.

Powder Coatings

The instant invention also pertains to powder coating formulations which require resistance to photodegradation. Resin systems which would be applicable include glycidyl methacrylate or acrylate-functional acrylic or acrylic hybrids, crosslinked with diacids or anhydrides; acid or anhydride functional acrylic or polyester resins crosslinked with TGIC; hydroxyl functional acrylic or polyester resins crosslinked with isocyanates. The stabilized coating may be a single layer applied to a substrate, or may be a clearcoat applied over a water borne or solvent borne basecoat.

The stabilized coating may also contain a UV absorber, consisting of one of the aforementioned compounds.

Radiation-Cured Systems

The instant invention also pertains to radiation-cured coating systems. These systems comprise:
a. Ethylenically unsaturated polymerizable compounds
b. At least one photoinitiator
c. One or more of the instant stabilizing compounds The coating composition may also include a UV absorbing stabilizer, represented by one of the classes mentioned.

The coating may also include pigments or other colorants designed to provide opacity or aesthetic properties.

The ethylenically unsaturated polymerizable compounds can contain one or more than one olefinic double bond. They may be low molecular (monomeric) or high molecular (oligomeric) compounds.

Typical examples of monomers containing one double bond are alkyl or hydroxyalkyl acrylates or methacrylates, for example methyl, ethyl, butyl, 2-ethylhexyl and 2-hydroxyethyl acrylate, isobornyl acrylate, and methyl and ethyl methacrylate. Further examples of these monomers are acrylonitrile, acrylamide, methacrylamide, N-substituted (meth) acrylamides, vinyl esters such as vinyl acetate, vinyl ethers such as isobutyl vinyl ether, styrene, alkylstyrenes, halostyrenes, N-vinylpyrrolidone, vinyl chloride and vinylidene chloride.

Examples of monomers containing more than one double bond are ethylene glycol diacrylate, propylene glycol diacrylate, neopentyl glycol diacrylate, hexamethylene glycol diacrylate, bisphenol A diacrylate, 4,4'-bis(2-acryloyloxyethoxy)diphenylpropane, trimethylolpropane triacrylate, pentaerythritol triacrylate and tetraacrylate, pentaerythritol divinyl ether, vinyl acrylate, divinyl benzene, divinyl succinate, diallyl phthalate, triallyl phosphate, triallyl isocyanurate or tris(2-acryloylethyl)isocyanurate. Examples of high molecular weight (oligomeric) polyunsaturated compounds are acrylated epoxy resins, acrylated polyethers, acrylated polyurethanes and acrylated polyesters. Further examples of unsaturated oligomers are unsaturated polyester resins, which are usually prepared from maleic acid, phthalic acid and one or more diols and which have molecular weights of greater than about 500. Unsaturated oligomers of this type are also known as prepolymers.

Typical examples of unsaturated compounds are esters of ethylenically unsaturated carboxylic acids and polyols or polyepoxides, and polymers containing ethylenically unsaturated groups in the chain or in side groups, including unsaturated polyesters, polyamides and polyurethanes and copolymers thereof, polybutadiene and butadiene copolymers, polyisoprene and isoprene copolymers, polymers and copolymers containing (meth)acrylic groups in side-chains, as well as mixtures of one or more than one such polymer.

Illustrative examples of unsaturated carboxylic acids are acrylic acid, methacrylic acid, crotonic acid, itaconic acid, cinnamic acid, unsaturated fatty acids such as linolenic acid or oleic acid. Acrylic and methacrylic acid are preferred.

Suitable polyols are aromatic and, preferably, aliphatic and cycloaliphatic polyols. Aromatic polyols are typically hydroquinone, 4,4'-dihydroxydiphenyl, 2,2-bis(4-hydroxyphenyl) propane, as well as novolacs and cresols. Polyepoxides include those based on the cited polyols, preferably on the aromatic polyols and epichlorohydrin. Further suitable polyols are polymers and copolymers which contain hydroxyl groups in the polymer chain or in side groups, for example polyvinyl alcohol and copolymers thereof or hydroxyalkyl polymethacrylates or copolymers thereof. Other suitable polyols are oligoesters carrying hydroxyl end groups.

Illustrative examples of aliphatic and cycloaliphatic polyols are alkylenediols containing preferably 2 to 12 carbon atoms, including ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably 200 to 1500,1,3-cyclopentanediol, 1,2-, 1,3- or 1,4-cyclohexanediol, 1,4-dihydroxymethylcyclohexane, glycerol, tris(☐-hydroxyethyl)amine, trimethylolethane, trimethylolpropane, pentaerythritol, dipentaerythritol and sorbitol.

The polyols may be esterified partially or completely with one or with different unsaturated carboxylic acids, in which case the free hydroxyl groups of the partial esters may be modified, for example etherified, or esterified with other carboxylic acids.

Illustrative examples of esters are: Trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentacrylate, dipentaerythritol hexacrylate, tripentaerythritol octacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentacrylate, sorbitol hexacrylate, oligoester acrylates and methacrylates, glycerol di- and -triacrylate, 1,4-cyclohexanediacrylate, bisacrylates and bis-methacrylates of polyethylene glycol having molecular weights of 200 to 1500, or mixtures thereof. Polyfunctional monomers and oligomers are available for example from UCB Chemicals, Smyrna, Ga., and Sartomer, Exton, Pa.

Suitable ethylenically unsaturated polymerizable compounds are also the amides of identical or different unsaturated carboxylic acids of aromatic, cycloaliphatic and aliphatic polyamines containing preferably 2 to 6, more particularly 2 to 4, amino groups. Exemplary of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, bis(β-aminoethyl) ether, diethylenetriamine, triethylenetetramine, bis(β-aminoethoxy)ethane or bis(β-aminopropoxy)ethane. Other suitable polyamines are polymers and copolymers which may contain additional amino groups in the side-chain and oligoamides containing amino end groups.

Exemplary of such unsaturated amides are: Methylenebisacrylamide, 1,6-hexamethylenebisacrylamide, diethylenetriaminetrismethacrylamide, bis(methacrylamidopropoxy)ethane, β-methacrylamidoethylmethacrylate, N-[(β-hydroxyethoxy)ethyl]acrylamide.

Suitable unsaturated polyesters and polyamides are derived typically from maleic acid and diols or diamines. Maleic acid can be partially replaced by other dicarboxylic acids such as fumaric acid, itaconic acid, citraconic acid, mesaconic acid or chloromaleic acid. To control the reactivity of the polyester and to influence the crosslinking density and hence the product properties, it is possible to use in addition to the unsaturated dicarboxylic acids different amounts of saturated dicarboxylic acids such as phthalic acid, isophthalic acid, terephthalic acid, tetrahydrophthalic acid, succinic acid or adipic acid. The unsaturated polyesters can be used together with ethylenically unsaturated comonomers such as styrene. The polyesters and polyamides can also be derived from dicarboxylic acids and ethylenically unsaturated diols or diamines, especially from those with long chains containing typically from 6 to 20 carbon atoms. Polyurethanes are typically those derived from saturated or unsaturated diisocyanates and unsaturated and saturated diols.

Suitable polyester acrylates or acrylated polyesters are obtained by reacting oligomers, typically epoxides, urethanes, polyethers or polyesters, with acrylates such as hydroxyethyl acrylate or hydroxypropyl acrylate.

Polybutadiene and polyisoprene and copolymers thereof are known. Suitable comonomers include olefins such as ethylene, propene, butene, hexene, (meth)acrylates, acrylonitrile, styrene or vinyl chloride. Polymers containing (meth) acrylate groups in the side-chain are also known. They may typically be reaction products of epoxy resins based on novolak with (meth)acrylic acid, homo- or copolymers of polyvinyl alcohol or their hydroxyalkyl derivatives which are esterified with (meth)acrylic acid or homo- and copolymers of (meth)acrylates which are esterified with hydroxyalkyl (meth)acrylates.

Preferred monomers are typically alkyl- or hydroxyalkyl acrylates or methacrylates, styrene, ethylene glycol diacrylate, propylene glycol diacrylate, neopentyl glycol diacrylate, hexamethylene glycol diacrylate or bisphenol A diacrylate, 4,4'-bis(2-acryloyloxyethoxy)diphenylpropane, trimethylolpropane triacrylate, pentaerythritol triacrylate or tetraacrylate, preferably acrylates, styrene, hexamethylene glycol or bisphenol A diacrylate, 4,4'-bis(2-acryloyloxyethoxy)diphenylpropane or trimethylolpropane triacrylate.

Particularly preferred (oligomeric) polyunsaturated compounds are polyester acrylates or unsaturated polyester resins which are prepared from maleic acid, fumaric acid, phthalic acid and one or more than one diol, and which typically have molecular weights from about 500 to 3000.

Preferred unsaturated carboxylic acids are acrylic acid and methacrylic acid.

The photopolymerizable compounds are used by themselves or in any desired mixtures. It is preferred to use mixtures of polyol(meth)acrylates.

Binders may also be added to the unsaturated photopolymerizable compounds. The addition of binders is particularly useful if the photopolymerizable compounds are liquid or viscous substances. The amount of binder may be from 5-95, preferably 10-90 and, most preferably, 40-90, percent by weight, based on the entire composition. The choice of binder will depend on the field of use and the desired properties therefore, such as the ability of the compositions to be developed in aqueous and organic solvent systems, adhesion to substrates and susceptibility to oxygen.

Suitable binders are typically polymers having a molecular weight of about 5,000 to 2,000,000, preferably 10,000 to 1,000,000. Illustrative examples are: Homo- and copolymers of acrylates and methacrylates, including copolymers of methyl methacrylate/ethyl acrylate/methacrylic acid, poly (alkylmethacrylates), poly(alkylacrylates); cellulose esters and ethers such as cellulose acetate, cellulose acetobutyrate, methyl cellulose, ethyl cellulose; polyvinyl butyral, polyvinyl formal, cyclized rubber, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethylene adipamide), polyesters such as poly(ethylene glycol terephthalate) and poly (hexamethylene glycol succinate).

The unsaturated compounds can also be used in admixture with non-photopolymerizable film-forming components. These components may be physically drying polymers or solutions thereof in organic solvents, for example nitrocellulose or cellulose acetobutyrate. The photopolymerizable unsaturated monomers may be a component of a free radical-ionic curable blend, such as a free radical-cationic curable blend. Also of importance are systems that undergo both thermal and photo-induced curing cycles, such as are used in powder coatings, laminates, certain adhesives and conformal coatings.

Mixtures of a prepolymer with polyunsaturated monomers which, additionally contain a further unsaturated monomer are frequently used in paint systems. The prepolymer in this instance primarily determines the properties of the paint film and, by varying it, the skilled person can influence the properties of the cured film. The polyunsaturated monomer acts as crosslinking agent that renders the paint film insoluble. The mono-unsaturated monomer acts as reactive diluent with the aid of which the viscosity is lowered without having to use a solvent. Moreover, properties of the cured composition such as curing rate, crosslinking density and surface properties are dependent on the choice of monomer.

Unsaturated polyester resins are usually used in two-component systems, together with a mono-unsaturated monomer, preferably with styrene.

Binary electron-rich/electron-poor monomer systems are often employed in thick pigmented coatings. For example, vinyl ether/unsaturated polyester systems are employed in powder coatings and styrene/unsaturated polyester systems are used in gel coats.

A preferred process is that wherein the ethylenically unsaturated polymerizable compounds are a mixture of (i) at least one oligomeric compound and (ii) at least one monomer.

An interesting process is that wherein the ethylenically unsaturated polymerizable compounds are a mixture of (i) unsaturated polyesters, especially those that are prepared from maleic acid, fumaric acid and/or phthalic acid and one or more than one diol, and which have molecular weights of 500 to 3,000, and (ii) acrylates, methacrylates or styrene or combinations thereof.

An important process is also that wherein the ethylenically unsaturated polymerizable compounds are a mixture of (i) unsaturated polyesters and (ii) acrylates or methacrylates or combinations thereof.

Another interesting process is that wherein the ethylenically unsaturated polymerizable compounds are a mixture of (i) unsaturated polyester acrylates and (ii) acrylates or methacrylates or combinations thereof.

The amount of instant stabilizer compounds employed in the compositions of this invention are for example from about 0.001% to about 10% by weight, based on the weight of the composition and depending on the composition.

For example, the amount of the present stabilizers employed in body care products, household products, textiles and fabrics is from about 0.001% to about 10% by weight, or from about 0.001% to about 5% by weight, based on the weight of the composition.

The amount of instant stabilizer compounds employed in coatings is from about 0.1 to about 10% by weight, for example from about 0.2 to about 5% by weight, for example from about 0.5 to about 3% by weight based on the weight of the solvent-free binder. The binders can be dissolved or dispersed in customary organic solvents or in water or can be solvent-free.

If combinations of stabilizers are used, the sum of all light stabilizers is for example from about 0.2 to about 20% by weight, for instance from about 0.5 to about 5% by weight, based on the film-forming resin.

It is also contemplated that the instant compounds would find particular value when used with water soluble inks and related polar oriented utilities where the presence of the water solubilizing groups would provide for better compatibility and properties related to such aqueous environments.

Other materials that are stabilized according to the instant invention include recording materials such as photographic reproductions or reprographic materials. The novel recording materials also include, for example, pressure-sensitive copying systems, microcapsule photocopier systems, heat-sensitive copier systems, photographic material and ink-jet printing. The various components of ink jet media are disclosed for example in U.S. Pat. Nos. 4,503,111, 4,575,465, 4,935,307, 5,206,071, 6,096,826 and 6,127,037 and U.S. app. No. 60/406,441, filed Aug. 28, 2002, the relevant parts of which are hereby incorporated by reference.

The ink jet ink according to this invention comprises about 0.01 to about 30% by weight, for example about 0.1 to about 20% by weight, of at least one present sterically hindered amine stabilizer, based on the weight of the ink jet ink.

The ink jet recording material according to this invention comprises about 1 to about 10000 mg/m$^2$, for example about 50 to about 2000 mg/m$^2$, of at least one present sterically hindered amine stabilizer.

The present sterically hindered amine stabilizers are preferably added to casting or coating dispersions which are applied by customary techniques to the support of the ink jet recording material, or they can be absorbed onto the material from an aqueous or organic solution. If the recording material contains more than one layer, the compounds according to this invention can be added to one layer or can be distributed over a plurality of layers, wherein they can be applied to a plurality of layers in the same or different concentrations.

The present sterically hindered amine stabilizers are preferably used in ink jet inks or recording materials, but may also be incorporated in ink compositions for felt-tipped pens, ink pads, fountain pens, and pen plotters, as well as for offset, book, flexographic and intaglio printing, and also for typewriter ribbons for dot matrix and calligraphic printing. The sterically hindered amine stabilizers can further be used in silver halide photographic materials as well as in recording materials for pressure-sensitive copying systems, microcapsule photocopier systems, heat-sensitive copier systems, dye diffusion transfer printing, thermal wax transfer printing and dot matrix printing, and for use with electrostatic, electrographic, electrophoretic, magnetographic and laser-electrophotographic printers, recorders or plotters.

Amongst the printers used for ink jet printing, a distinction is usually made between continuous and drop-on-demand printers. The ink jet system according to this invention is suited for use with both type of printers.

The ink compositions according to the novel ink jet system are preferably water borne inks and may contain water soluble solvents such as ethylene glycol, diethylene glycol, triethylene glycol or higher ethylene glycols, propylene glycol, 1,4-butanediol, or ethers of such glycols, thiodiglycol, glycerol and the ethers and esters thereof, polyglycerol, mono-, di- and triethanolamine, propanolamine, dimethyl formamide, dimethyl sulfoxide, dimethyl acetamide, N-methylpyrrolidone, 1,3-dimethylimidazolidone, methanol, ethanol, isopropanol, n-propanol, diacetone alcohol, acetone, methyl ethyl ketone or propylene carbonate.

The ink compositions according to the novel ink jet system preferably contain water soluble dyes, such as those known for dyeing natural fibres. These can, for example, be acid dyes, direct dyes, reactive dyes, mono-, di- or polyazo dyes, triphenylmethane dyes, xanthene dyes or phtalocyanine dyes. Specific examples of such dyes are Food Black 2, Direct Black 19, Direct Black 38, Direct Black 168, Sulphur Black 1, Acid Red 14, Acid Red 35, Acid Red 52, Acid Red 249, Direct Red 227, Reactive Red 24, Reactive Red 40, Reactive Red 120, Reactive Red 159, Reactive Red 180, Acid Yellow 17, Acid Yellow 23, Direct Yellow 86, Direct Yellow 132, Acid blue 9, Acid Blue 185, Direct Blue 86, Direct Blue 199, copper phtalocyanines and the azo dyes listed in EP-A-366 221.

The ink compositions according to the invention may be nonaqueous and consist of a solution of dyes in an organic solvent or a mixture of organic solvents. Examples of solvents used for this purpose are alkyl carbitols, alkylcellosolves, dialkylformamides, dialkylacetamides, alcohols, acetone, methylethylketone, diethylketone, methyl isobutyl ketone, diisopropyl ketone, dibutyl ketone, dioxane, ethyl butyrate, ethyl isovalerate, diethyl malonate, diethyl succinate, butyl acetate, triethyl phosphate, ethylglycol acetate, toluene, xylene, tetralin or petroleum fractions. Example of solid waxes as solvents, which, as an ink carrier, must first be heated, are stearic or palmiric acid. Solvent based inks contain dyes soluble therein, for example Solvent Red, Solvent Yellow, Solvent Orange, Solvent Blue, Solvent Green, Solvent Violet, Solvent Brown or Solvent Black.

The ink compositions according to the novel ink jet system may also contain minor amounts of conventional modifiers such as binders, surfactants, biocides, corrosion inhibitors, sequestrants, pH buffers or conductivity additives. They may also contain further light stabilizers or UV absorbers, including the compounds disclosed in U.S. Pat. Nos. 5,073,448, 5,089,050, 5,096,489, 5,124,723, 5,098,477 and 5,509,957.

The ink compositions according to the invention may also consist of more than one phase. Ink compositions that consist of an aqueous phase in which the dye is dissolved and a dispersed oil phase that contains an UV absorber and/or an antioxidant are for example disclosed in JP-A-01 170 675, JP-A-01 182 379, JP-A-01 182 380, JP-A-01 182 381, JP-A-01 193 376. Oil soluble dyes can be dissolved in an oil together with UV absorbers and/or antioxidants. The oil is either emulsified or dispersed in an aqueous phase as described, inter alia, in JP-A-01170674 and JP-A-01170672.

Further suited ink jet ink compositions are described in EP-A-672 538, pages 3 to 6.

The recording materials according to the novel ink jet system consist of a substrate having a surface which is printable by means of an ink jet. The substrate is usually plain paper or polyolefin-laminated paper or a plastic sheet and is usually coated with at least one layer which is able to absorb ink. The substrate preferably has a thickness of 80 to 250 µm.

Uncoated paper might also be used. In this case, the paper acts simultaneously as substrate and ink absorbing layer. Materials made of cellulosic fibers and textile fibers materials such as cotton fabrics or blends of cotton and polyacrylamide or polyester, which might contain the present sterically hindered amine light stabilizers, can also be used as printing materials.

The recording materials may also be transparent, as in the case of overhead projection transparencies.

The present sterically hindered amine stabilizers can be incorporated in the substrate during production thereof, conveniently by addition to the pulp during paper manufacture. Another method of application consists in spraying the substrate with a solution of the present sterically hindered amine stabilizers in water or in a readily volatile organic solvent. The use of emulsions or dispersions is also possible.

Usually, however, at least one coating composition with high dye affinity is coated onto the substrate and, in this case, the present sterically hindered amines are added to at least one of the said coating compositions. Typical coating compositions comprise, for example, a solid filler, a binder and conventional additives.

Example of suitable fillers are $SiO_2$, kaolin, talc, clay, calcium silicate, magnesium silicate, aluminium silicate, gypsum, zeolites, bentonite, diatomaceous earth, vermiculite, starch or the surface modified $SiO_2$ described in JP-A-60 260 377. Small amounts of white pigments, for example titanium dioxide, barytes, magnesium oxide, lime, chalk or magnesium carbonate, can be used with the filler in the coating composition, provided they do not significantly lower the print density of the ink jet prints.

The present sterically hindered amines may advantageously be employed in a nanoporous or microporous ink jet material.

Coating compositions which are intended for transparent, projectable recording materials must not contain any light-scattering particles, such as pigments and fillers.

The binder binds the fillers to one another and to the substrate. Typical conventional binders are water soluble polymers such as polyvinyl alcohol, partially hydrolysed polyvinyl acetate, cellulose and cellulose derivatives such as hydroxyethyl cellulose, polyvinyl pyrrolidone and copolymers thereof, polyethylene oxide, salts of polyacrylic acid, sodium alginate, starch and starch derivatives, Na alginate, polyethylene imine, polyvinylpyridinium halide, gelatines and gelatine derivatives such as phthaloyl gelatines, casein, vegetable gum, dextrin, albumin, dispersions and polyacrylates or acrylate/methacrylate copolymers, lattices of natural or synthetic rubber, poly(meth)acrylamide, polyvinyl ethers, polyvinyl esters, copolymers of maleic acid, melamine resins, urea resins, water soluble polyurethanes and polyesters, or the chemically modified polyvinyl alcohols disclosed in JP-A-61 134 290 or JP-A-61 134 291.

An additional dye receptor or a mordant which enhances the fixation of the dye to the coating may be added to the binder. Dye receptors for acid dyes are cationic or amphoteric. The cationic mordants can be soluble or dispersible in water. Exemplary cationic mordants are polymeric ammonium compounds such as polyvinylbenzyldi- or trialkylammonium compounds, optionally quaternized poly(di)allylammonium compounds, polymeth acryloxyethyldimethylhydroxyethylammonium chloride, polyvinylbenzylmethylimidazolium chloride, polyvinylbenzylpicolinium chloride or polyvinylbenzyltributylammonium chloride. Further examples are basic polymers such as poly(dimethylaminoethyl)methacrylate, polyalkylenepolyamines and their condensation products with dicyanodiamide, amine/epichlorohydrin polycondensates or the compounds disclosed in JP-A-57-36692, 57-64591, 57-187289, 57-191084, 58-177390, 58-208357, 59-20696, 59-33176, 59-96987, 59-198188, 60-49990, 60-71796, 60-72785, 60-161188, 60-187 582, 60-189481, 60-189482, 61-14979, 61-43593, 61-57379, 61-57380, 61-58788, 61-61887, 61-63477, 61-72581, 61-95977, 61-134291 or in U.S. Pat. Nos. 4,547,405 and 4,554,181 as well as in DE-A-3417582 and EP-B-609 930. The mordants used can also be compounds containing phosphonium groups (EP-B-609 930) as well as ground cationic ion exchange resins which are introduced in the mordant layer in a finely divided form. Further suitable cationic mordants are described in U.S. Pat. No. 6,102,997, pages 12 to 17. The cationic mordants can be soluble or dispersible in water and have an average molecular weight (weight average) of preferably at least 2,000 and, in particular, at least 20,000.

Besides the dye acceptor layer(s), the ink jet recording material might comprise other layers on the ink receiving side, which are intended, for example, for providing scratch resistance, absorbing water or controlling whiteness and/or glossiness. The backside of the substrate might also be coated with at least one binder layer, in order to prevent buckling of the recording material.

The ink jet recording material might also contain a number of other additives such as antioxidants, further light stabilizers (also including UV absorbers), viscosity improvers, fluorescent whitening agents, biocides, wetting agents, emulsifiers and spacers.

Suitable spacers are in particular spherical, have an average diameter of 1 to 50 µm, and in particular 5 to 20 µm, and have a narrow particle size distribution. Suitable spacers consist, for example, of polymethylmethacrylate, polystyrene, polyvinyl toluene, silicon dioxide and insoluble starch.

Illustrative examples of particularly suitable antioxidants are sterically hindered phenols, hydroquinones and hydroquinone ethers, for example the antioxidants disclosed in GB-A-2 088 777 or JP-A-60-72785, JP-A-0-72786 and JP-A-60-71796.

Illustrative examples of particularly suitable light stabilizers are organic nickel compounds and sterically hindered amines, for example the light stabilizers disclosed in JP-A-58-152072, 61-146591, 61-163886, 60-72785 and 61-146591 or in EP 373 573, 685 345 and 704 316, GB-A-2 088 777, JP-A-59-169883 and 61-177279.

Suitable UV absorbers are disclosed, inter alia, in Research Disclosure No. 24239 (1984) page 284, 37254 part VIII (1995) page 292, 37038 part X (1995) page 85 and 38957 part VI (1996), GB-A-2 088 777, EP 280 650, EP 306 083 and EP 711 804. These compounds are preferably introduced into the layer(s) farthest from the support. In a particular embodiment, the UV absorbers are contained in a layer above the layer(s) containing the present sterically hindered amines. Suitable UV absorbers for concurrent use with a present sterically hindered amines in recording materials for ink jet printing are in particular those of the 2'-hydroxyphenyl-benzotriazole and 2'-hydroxyphenyltriazine class and, most particularly, 2-(2'-hydroxy-3',5'-di-tert-amylphenyl)benzotriazole and 2-(2'-hydroxy-3'-tert-butyl-5'-polyglycolpropionate-phen-yl)benzotriazole. Further examples of particularly suited UV absorbers are listed in U.S. Pat. No. 6,102,997 pages 18-19. The UV absorbers can be soluble or insoluble in water and added to the coating composition as dispersion or emulsion, optionally together with high-boiling solvents, using suitable dispersing agents or emulsifiers. Suitable high boiling solvents are described in Research Disclosure No. 37254 part VIII (1995) page 292.

The binders in the individual layers, and in particular gelatines, can also be crosslinked by suitable compounds, so-called hardening agents, in order to improve the water and scratch resistance of the layers. Suitable hardening agents are described in Research Disclosure No. 37254 part IX (1995) page 294, 37038 part XII (1995) page 86 and 38957 part IIB (1996) page 599 et seq. The hardening agents are normally used in quantities of 0.005 to 10% by weight, and preferably 0.01 to 1% by weight, based on the binder to be hardened.

The ink jet recording material can be produced in one pass from the support material and a casting solution for each layer to be applied, by means of a cascade or curtain casting device of the kind known from the production of photographic silver halide materials. After the casting solution(s) has/have been cast on the support, the material is dried and is then ready for use. The individual layers have a dry layer thickness of 0.1 to 20 µm, and preferably 0.5 to 5 µm.

The present sterically hindered amines can be dissolved either directly in the ink or coating composition or added thereto in the form of an emulsion or suspension. As already mentioned, the present sterically hindered amines can be also applied to the recording material in a separate operation, alone or together with other already described components, as a solution in water or in a suitable organic solvent. Application can be made by spraying, by sizing in a sizing press, by a separate coating operation or by immersion in a vat. After subjecting the recording material to such an after treatment, an additional drying step is necessary.

The present photographic material can be a black and white or a color photographic material, color photographic material is preferred. Further details on the structure of color photographic material and the components which can be employed in such materials are described in U.S. Pat. No. 5,538,840 at column 27, line 25 to column 106, line 16. These relevant parts are incorporated herein by reference. Application of the instant novel compounds is essentially as described for UV absorbers or hindered amine stabilizers in U.S. Pat. No. 5,538,840.

Further important components, especially couplers, are described in U.S. Pat. No. 5,578,437.

Other articles which would benefit from the incorporation of the instant, water compatible hindered amine compounds include laminated articles as described in U.S. Pat. Nos. 6,268,415 and 6,191,199, the disclosures of which are hereby incorporated by reference. For example, laminated articles such as:

(a) Retroreflective Sheets and Signs and Conformable Marketing Sheets as seen in WO 97/42261; and U.S. Pat. No. 5,387,458 which is incorporated herein by reference;

(b) Solar Control Films of Various Construction as seen in British 2,012,668; European 355,962; and U.S. Pat. Nos. 3,290,203; 3,681,179; 3,776,805 and 4,095,013 which are incorporated herein by reference;

(c) Corrosion Resistant Silver Mirrors and Solar Reflectors as seen in U.S. Pat. No. 4,645,714 which is incorporated herein by reference;

(d) Reflective Print Labels as seen in U.S. Pat. No. 5,564,843 which is incorporated herein by reference;

(e) UV Absorbing Glasses and Glass Coatings as seen in U.S. Pat. Nos. 5,372,889; 5,426,204; 5,683,804 and 5,618,626 which are incorporated herein by reference;

(f) Electrochromic Devices as seen in European 752,612 A1; and U.S. Pat. Nos. 5,239,406; 5,523,877 and 5,770,114 which are incorporated herein by reference;

(g) Films/Glazings as seen in WO 92/01557; Japanese Nos. 75-33286; 93-143668; 95-3217 and 96-143831; and U.S. Pat. No. 5,643,676 which is incorporated herein by reference;

(h) Windscreens and Intermediate Layers as seen in Japanese Nos. 80-40018; 90-192118; 90-335037; 90-335038; 92-110128 and 94-127591; and (i) Optical Films as seen in WO 97/32225; and U.S. Pat. Nos. 4,871,784 and 5,217,794 which are incorporated herein by reference.

As mentioned, the stabilized compositions of the invention may optionally also contain other conventional stabilizers. For example, the compositions of this invention may contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1-methylundec-1-yl)phenol, 2,4-dimethyl-6-(1-methylheptadec-1-yl) phenol, 2,4-dimethyl-6-(1-methyltridec-1-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, 6-tocopherol and mixtures thereof (Vitamin E).

1.5. Hydroxylated thiodiphenyl ethers, for example 2, 2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl) disulfide.

1.6. Alkylidenebisphenols, for example 2, 2'-methylenebis (6-tert-butyl-4-methylphenol), 2,2'-methylenebis(6-tert-butyl-4-ethylphenol), 2,2'-methylenebis[4-methyl-6-α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis [6-(α-methylbenzyl)-4-nonylphenol], 2,2'-methylenebis[6-(α,α-dimethylbenzyl)-4-nonylphenol], 4,4'-methylenebis(2, 6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3-tert-butyl-4-hydroxyphenyl) butyrate], bis(3-tert-butyl-4-hydroxy-5-methyl-phenyl)dicyclopentadiene, bis[2-(3'tert-butyl-2-hydroxy-5-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy-2-methylphenyl)-4-n-dodecylmercaptobutane, 1,1, 5,5-tetra-(5-tert-butyl-4-hydroxy-2-methylphenyl)pentane.

1.7. Benzyl compounds, for example 3, 5,3',5'-tetra-tert-butyl-4,4'-dihydroxydibenzyl ether, octadecyl-4-hydroxy-3, 5-dimethylbenzylmercaptoacetate, tridecyl-4-hydroxy-3,5-di-tert-butylbenzylmercaptoacetate, tris(3,5-di-tert-butyl-4-hydroxybenzyl)amine, 1,3,5-tri-(3,5-di-tert-butyl-4-hydroxybenzyl)-2,4,6-trimethylbenzene, di-(3,5-di-tert-butyl-4-hydroxybenzyl)sulfide, 3,5-di-tert-butyl-4-hydroxybenzyl-mercapto-acetic acid isooctyl ester, bis-(4-tert-butyl-3-hydroxy-2,6-dimethylbenzyl)dithiol terephthalate, 1,3,5-tris-(3,5-di-tert-butyl-4-hydroxybenzyl) isocyanurate, 1,3,5-tris-(4-tert-butyl-3-hydroxy-2,6-dimethylbenzyl)isocyanurate, 3,5-di-tert-butyl-4-hydroxybenzyl-phosphoric acid dioctadecyl ester and 3,5-di-tert-butyl-4-hydroxybenzyl-phosphoric acid monoethyl ester, calcium-salt.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl) malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2, 3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris-(3,5-di-tert-butyl-4-hydroxy-benzyl)isocyanurate, 1,3,5-tris(4-tert-butyl-3-hydroxy-2,6-dimethylbenzyl)isocyanurate, 2,4, 6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxy-lauric acid anilide, 4-hydroxy-stearic acid anilide, 2,4-bis-octylmercapto-6-(3,5-tert-butyl-4-hydroxyanilino)-s-triazine and octyl-N-(3,5-di-tert-butyl-4-hydroxyphenyl)-carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexane-diol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl] propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyl-diphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV Absorbers and Light Stabilizers 2.1. 2-(2-Hydroxyphenyl)-2H-benzotriazoles, for example known commercial hydroxyphenyl-2H-benzotriazoles and benzotriazoles as disclosed in, U.S. Pat. Nos. 3,004,896; 3,055,896; 3,072,585; 3,074,910; 3,189,615; 3,218,332; 3,230,194; 4,127,586; 4,226,763; 4,275,004; 4,278,589; 4,315,848; 4,347,180; 4,383,863; 4,675,352; 4,681,905; 4,853,471; 5,268,450; 5,278,314; 5,280,124; 5,319,091; 5,410,071; 5,436,349; 5,516,914; 5,554,760; 5,563,242; 5,574,166; 5,607,987, 5,977,219 and 6,166,218 such as 2-(2-hydroxy-5-methylphenyl)-2H-benzotriazole, 2-(3,5-di-t-butyl-2-hydroxyphenyl)-2H-benzotriazole, 2-(2-hydroxy-5-t-butylphenyl)-2H-benzotriazole, 2-(2-hydroxy-5-t-octylphenyl)-2H-benzotriazole, 5-chloro-2-(3,5-di-t-butyl-2-hydroxyphenyl)-2H-benzotriazole, 5-chloro-2-(3-t-butyl-2-hydroxy-5-methylphenyl)-2H-benzotriazole, 2-(3-sec-butyl-5-t-butyl-2-hydroxyphenyl)-2H-benzotriazole, 2-(2-hydroxy-4-octyloxyphenyl)-2H-benzotriazole, 2-(3,5-di-t-amyl-2-hydroxyphenyl)-2H-benzotriazole, 2-(3,5-bis-α-cumyl-2-hydroxyphenyl)-2H-benzotriazole, 2-(3-t-butyl-2-hydroxy-5-(2-(ω-hydroxy-octa-(ethyleneoxy)carbonylethyl)-, phenyl)-2H-benzotriazole, 2-(3-dodecyl-2-hydroxy-5-methylphenyl)-2H-benzotriazole, 2-(3-t-butyl-2-hydroxy-5-(2-octyloxycarbonyl)ethylphenyl)-2H-benzotriazole, dodecylated 2-(2-hydroxy-5-methylphenyl)-2H-benzotriazole, 2-(3-t-butyl-2-hydroxy-5-(2-octyloxycarbonylethyl) phenyl)-5-chloro-2H-benzotriazole, 2-(3-tert-butyl-5-(2-(2-ethylhexyloxy)-carbonylethyl)-2-hydroxyphenyl)-5-chloro-2H-benzotriazole, 2-(3-t-butyl-2-hydroxy-5-(2-methoxycarbonylethyl)phenyl)-5-chloro-2H-benzotriazole, 2-(3-t-butyl-2-hydroxy-5-(2-methoxycarbonylethyl)phenyl)-2H-benzotriazole, 2-(3-t-butyl-5-(2-(2-ethylhexyloxy)carbonylethyl)-2-hydroxyphenyl)-2H-benzotriazole, 2-(3-t-butyl-2-hydroxy-5-(2-isooctyloxycarbonylethyl)phenyl-2H-benzotriazole, 2,2'-methylene-bis(4-t-octyl-(6-2H-benzotriazol-2-yl)phenol), 2-(2-hydroxy-3-α-cumyl-5-t-octylphenyl)-2H-benzotriazole, 2-(2-hydroxy-3-t-octyl-5-α-cumylphenyl)-2H-benzotriazole, 5-fluoro-2-(2-hydroxy-3,5-di-α-cumyl-phenyl)-2H-benzotriazole, 5-chloro-2-(2-hydroxy-3,5-di-α-cumylphenyl)-2H-benzotriazole, 5-chloro-2-(2-hydroxy-3-α-cumyl-5-t-octylphenyl)-2H-benzotriazole, 2-(3-t-butyl-2-hydroxy-5-(2-isooctyloxycarbonylethyl)phenyl)-5-chloro-2H-benzotriazole, 5-trifluoromethyl-2-(2-hydroxy-3-α-cumyl-5-t-octylphenyl)-2H-benzotriazole, 5-trifluoromethyl-2-(2-hydroxy-5-t-octylphenyl)-2H-benzotriazole, 5-trifluoromethyl-2-(2-hydroxy-3,5-di-t-octylphenyl)-2H-benzotriazole, methyl 3-(5-trifluoromethyl-2H-benzotriazol-2-yl)-5-t-butyl-4-hydroxyhydrocinnamate, 5-butylsulfonyl-2-(2-hydroxy-3-α-cumyl-5-t-octylphenyl)-2H-benzotriazole, 5-trifluoromethyl-2-(2-hydroxy-3-α-cumyl-5-t-butylphenyl)-2H-benzotriazole, 5-trifluoromethyl-2-(2-hydroxy-3,5-di-t-butylphenyl)-2H-benzotriazole, 5-trifluoromethyl-2-(2-hydroxy-3,5-di-α-cumylphenyl)-2H-benzotriazole, 5-butylsulfonyl-2-(2-hydroxy-3,5-di-t-butylphenyl)-2H-benzotriazole and 5-phenylsulfonyl-2-(2-hydroxy-3,5-di-t-butylphenyl)-2H-benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tert-butylphenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates and malonates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline, Sanduvor® PR25, dimethyl p-methoxybenzylidenemalonate (CAS# 7443-25-6), and Sanduvor® PR31, di-(1,2,2,6,6-pentamethylpiperidin-4-yl) p-methoxybenzylidenemalonate (CAS #147783-69-5).

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amine stabilizers, for example 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, bis(2,2,6,6-tetramethyl-4-piperidyl) sebacate, bis(2,2,6,6-tetramethyl-4-piperidyl) succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4,5]decan-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)-hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-amino-propylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4,5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxy-methylenemalonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

The sterically hindered amine may also be one of the compounds described in U.S. Pat. No. 5,980,783, the relevant parts of which are hereby incorporated by reference, that is compounds of component (I-a), I-b), I-c), I-d), I-e), I-f), I-g), I-h), I-i), I-j), I-k) or I-l), in particular the light stabilizer 1-a-1, 1-a-2, 1-b-1, 1-c-1, 1-c-2, 1-d-1, 1-d-2, 1-d-3, 1-e-1, 1-f-1, 1-g-1, 1-g-2 or 1-k-1 listed on columns 64-72 of said U.S. Pat. No. 5,980,783.

The sterically hindered amine may also be one of the compounds described in EP 782994, for example compounds as described in claims 10 or 38 or in Examples 1-12 or D-1 to D-5 therein.

2.7. Sterically hindered amines substituted on the N-atom by a hydroxy-substituted alkoxy group, for example compounds such as 1-(2-hydroxy-2-methylpropoxy)-4-octadecanoyloxy-2,2,6,6-tetramethylpiperidine, 1-(2-hydroxy-2-methylpropoxy)-4-hexadecanoyloxy-2,2,6,6-tetramethylpiperidine, the reaction product of 1-oxyl-4-hydroxy-2,2,6,6-tetramethylpiperidine with a carbon radical from t-amylalcohol, 1-(2-hydroxy-2-methylpropoxy)-4-hydroxy-2,2,6,6-tetramethylpiperidine, 1-(2-hydroxy-2-methylpropoxy)-4-oxo-2,2,6,6-tetramethylpiperidine, bis(1-(2-hydroxy-2-methylpropoxy)-2,2,6,6-tetramethylpiperidin-4-yl) sebacate, bis(1-(2-hydroxy-2-methylpropoxy)-2,2,6,6-tetramethylpiperidin-4-yl) adipate, bis(1-(2-hydroxy-2-methylpropoxy)-2,2,6,6-tetramethylpiperidin-4-yl) succinate, bis(1-(2-hydroxy-2-methylpropoxy)-2,2,6,6-tetramethylpiperidin-4-yl)glutarate and 2,4-bis{N-[1-(2-hydroxy-2-methylpropoxy)-2,2,6,6-tetramethylpiperidin-4-yl]-N-butylamino}-6-(2-hydroxyethyl-amino)-s-triazine.

2.8. Oxamides, for example 4, 4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.9. Tris-aryl-o-hydroxyphenyl-s-triazines, for example known commercial tris-aryl-o-hydroxyphenyl-s-triazines and triazines as disclosed in, WO 96/28431 and U.S. Pat. Nos. 3,843,371; 4,619,956; 4,740,542; 5,096,489; 5,106,891; 5,298,067; 5,300,414; 5,354,794; 5,461,151; 5,476,937; 5,489,503; 5,543,518; 5,556,973; 5,597,854; 5,681,955; 5,726,309; 5,736,597; 5,942,626; 5,959,008; 5,998,116; 6,013,704; 6,060,543; 6,187,919; 6,242,598 and 6,255,483, for example 4,6-bis-(2,4-dimethylphenyl)-2-(2-hydroxy-4-octyloxyphenyl)-s-triazine, Cyasorb® 1164, Cytec Corp, 4,6-bis-(2,4-dimethylphenyl)-2-(2,4-dihydroxyphenyl)-s-triazine, 2,4-bis(2,4-dihydroxyphenyl)-6-(4-chlorophenyl)-s-triazine, 2,4-bis[2-hydroxy-4-(2-hydroxyethoxy)phenyl]-6-(4-chlorophenyl)-s-triazine, 2,4-bis[2-hydroxy-4-(2-hydroxy-4-(2-hydroxyethoxy)phenyl]-6-(2,4-dimethylphenyl)-s-triazine, 2,4-bis[2-hydroxy-4-(2-hydroxyethoxy)phenyl]-6-(4-bromophenyl)-s-triazine, 2,4-bis[2-hydroxy-4-(2-acetoxyethoxy)-phenyl]-6-(4-chlorophenyl)-s-triazine, 2,4-bis(2,4-dihydroxyphenyl)-6-(2,4-dimethylphenyl)-s-triazine, 2,4-bis(4-biphenylyl)-6-(2-hydroxy-4-octyloxycarbonylethylideneoxyphenyl)-s-triazine, 2-phenyl-4-[2-hydroxy-4-(3-sec-butyloxy-2-hydroxypropyloxy)phenyl]-6-[2-hydroxy-4-(3-sec-amyloxy-2-hydroxypropyloxy)phenyl]-s-triazine, 2,4-bis(2,4-dimethylphenyl)-6-[2-hydroxy-4-(3-benzyloxy-2-hydroxypropyloxy)phenyl]-s-triazine, 2,4-bis(2-hydroxy-4-n-butyloxyphenyl)-6-(2,4-di-n-butyloxyphenyl)-s-triazine, 2,4-bis(2,4-dimethylphenyl)-6-[2-hydroxy-4-(3-nonyloxy*-2-hydroxypropyloxy)-5-α-cumylphenyl]-s-triazine (* denotes a mixture of octyloxy, nonyloxy and decyloxy groups), methylenebis-{2,4-bis(2,4-dimethylphenyl)-6-[2-hydroxy-4-(3-butyloxy-2-hydroxypropoxy)phenyl]-s-triazine}, methylene bridged dimer mixture bridged in the 3:5', 5:5' and 3:3' positions in a 5:4:1 ratio, 2,4,6-tris(2-hydroxy-4-isooctyloxycarbonylisopropylideneoxy-phenyl)-s-triazine, 2,4-bis(2,4-dimethylphenyl)-6-(2-hydroxy-4-hexyloxy-5-α-cumylphenyl)-s-triazine, 2-(2,4,6-trimethylphenyl)-4,6-bis[2-hydroxy-4-(3-butyloxy-2-hydroxypropyloxy)phenyl]-s-triazine, 2,4,6-tris[2-hydroxy-4-(3-sec-butyloxy-2-hydroxypropyloxy)phenyl]-s-triazine, mixture of 4,6-bis-(2,4-dimethylphenyl)-2-(2-hydroxy-4-(3-dodecyloxy-2-hydroxypropoxy)-phenyl)-s-triazine and 4,6-bis-(2,4-dimethylphenyl)-2-(2-hydroxy-4-(3-tridecyloxy-2-hydroxypropoxy)-phenyl)-s-triazine, Tinuvin® 400, Ciba Specialty Chemicals Corp., 4,6-bis-(2,4-dimethylphenyl)-2-(2-hydroxy-4-(3-(2-ethylhexyloxy)-2-hydroxypropoxy)-phenyl)-s-triazine and 4,6-diphenyl-2-(4-hexyloxy-2-hydroxyphenyl)-s-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris (2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl) pentaerythritol diphosphite, bis(2,4,6-tris(tert-butylphenyl) pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-dibenzo[d,f][1,3,2]dioxaphosphepin, 6-fluoro-2,4,8,10-tetra-tert-butyl-12-methyl-dibenzo[d,g][1,3,2]dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite.

Especially preferred are the following phosphites:
Tris(2,4-di-tert-butylphenyl) phosphite, tris(nonylphenyl) phosphite,

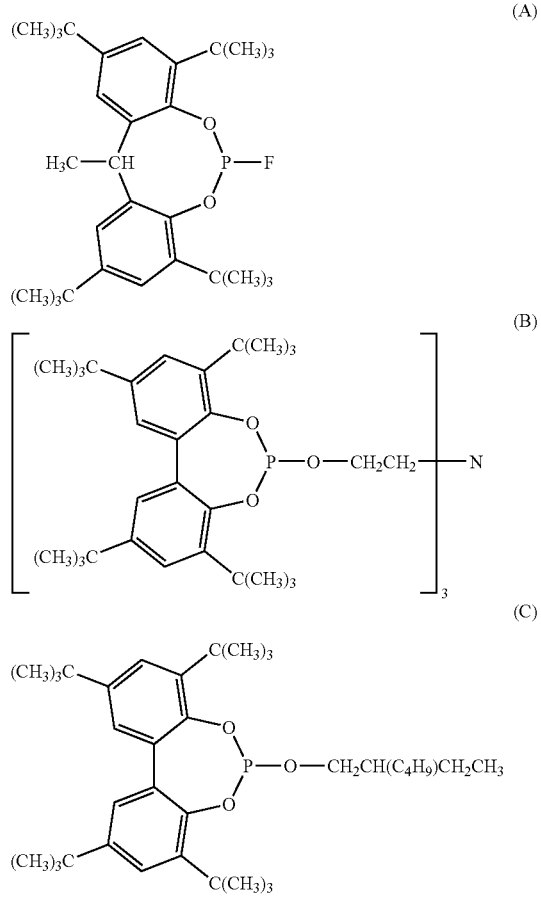

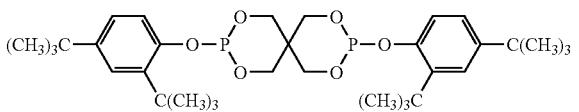

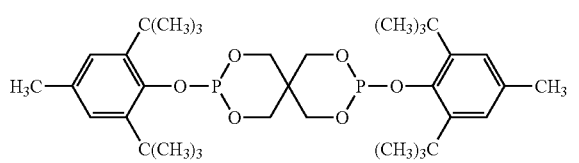

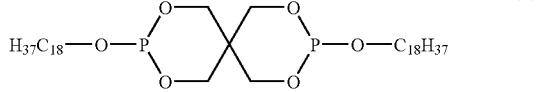

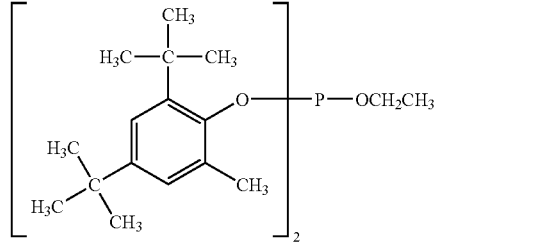

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxyl-amine, N-heptadecyl-N-octadecylhydroxylamine, N-methyl-N-octadecylhydroxylamine and the N,N-dialkylhydroxylamine derived from hydrogenated tallow amine.

6. Nitrones, for example N-benzyl-α-phenylnitrone, N-ethyl-α-methylnitrone, N-octyl-α-heptylnitrone, N-lauryl-α-undecylnitrone, N-tetradecyl-α-tridcylnitrone, N-hexadecyl-α-pentadecylnitrone, N-octadecyl-α-heptadecylnitrone, N-hexadecyl-α-heptadecylnitrone, N-ocatadecyl-α-pentadecylnitrone, N-heptadecyl-α-heptadecylnitrone, N-octadecyl-α-hexadecylnitrone, N-methyl-α-heptadecylnitrone and the nitrone derived from N,N-dialkylhydro-xylamine derived from hydrogenated tallow amine.

7. Amine oxides, for example amine oxide derivatives as disclosed in U.S. Pat. Nos. 5,844,029 and 5,880,191, didecyl methyl amine oxide, tridecyl amine oxide, tridodecyl amine oxide and trihexadecyl amine oxide.

8. Benzofuranones and indolinones, for example those disclosed in U.S. Pat. Nos. 4,325,863, 4,338,244, 5,175,312, 5,216,052, 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl]-benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, and 3-(2,3-dimethylphenyl)-5,7-di-tert-butyl-benzofuran-2-one.

9. Thiosynergists, for example dilauryl thiodipropionate or distearyl thiodipropionate.

10. Peroxide scavengers, for example esters of β-thiodipropionic acid, for example the lauryl, stearyl, myristyl or tridecyl esters, mercaptobenzimidazole or the zinc salt of 2-mercapto-benzimidazole, zinc dibutyldithiocarbamate, dioctadecyl disulfide, pentaerythritol tetrakis(β-dodecylmercapto)propionate.

11. Polyamide stabilizers, for example copper salts in combination with iodides and/or phosphorus compounds and salts of divalent manganese.

12. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, calcium stearate, zinc stearate, magnesium behenate, magnesium stearate, sodium ricinoleate and potassium palmitate, antimony pyrocatecholate or zinc pyrocatecholate.

13. Nucleating agents, for example inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

14. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

15. Dispersing Agents, such as polyethylene oxide waxes or mineral oil.

16. Other additives, for example plasticizers, lubricants, emulsifiers, pigments, dyes, optical brighteners, rheology additives, catalysts, flow-control agents, slip agents, crosslinking agents, crosslinking boosters, halogen scavengers, smoke inhibitors, flameproofing agents, antistatic agents, clarifiers such as substituted and unsubstituted bisbenzylidene sorbitols, benzoxazinone UV absorbers such as 2,2'-p-phenylene-bis(3,1-benzoxazin-4-one), Cyasorb® 3638 (CAS# 18600-59-4), and blowing agents.

The sterically hindered alkoxyamines and hydroxy substituted alkoxyamines of the present invention are prepared according to known methods, with the additional step of incorporating a water compatible or water soluble side chain.

The preparation of sterically hindered alkoxyamine stabilizers, also known as N-alkoxy hindered amines and NOR hindered amines or NOR hindered amine light stabilizers or NOR HALS, is disclosed for example in U.S. Pat. Nos. 5,004,770 and 5,096,950, the relevant disclosures of which are hereby incorporated by reference.

The preparation of sterically hindered hydroxy substituted alkoxyamine stabilizers, also known as hindered hydroxyalkoxyamine stabilizers, N-hydroxyalkoxy hindered amines, or NOrol HALS, is disclosed for example in U.S. Pat. Nos. 6,271,377, 6,392,041 and 6,376,584, the relevant disclosures of which are hereby incorporated by reference.

The following non-limiting examples further illustrate the present invention.

Test compounds:

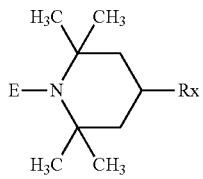

when E is 2-hydroxycyclohexyloxy or 2-hydroxy-2-methylpropoxy, $R_x$ is selected from the group consisting of
—$NH_2^+CH_2CH_2OH$ $Cl^-$, —$NHCH_2CH_2OH$, —$NH_3^{+-}OAc$, =NOH, —$NHCH(CH_3)COO^-K^+$, —$NHCH_2CH_2N(CH_3)_2^{+-}OAc$, —$NHCH_2CH_2SO_3^-K^+$, —$NHCH(COO^-K^+)CH_2CH_2SCH_3$, —$NHCH_2COO^-K^+$, —$NHCOCH_2OH$, —$NHCOCH_2NHCOCH_3$, —$NHCH_2CH_2CH_2SO_3H$, —$OCH_2CH_2OH$, —$OCH(CH_3)COO^-K^+$, —$OCH_2CH_2N(CH_3)_2^{+-}OAc$, —$OCH_2CH_2SO_3^-K^+$, —$OCH(COO^-K^+)CH_2CH_2SCH_3$, —$OCH_2COO$ $K^+$, —$OCOCH_2OH$, —$OCOCH_2NHCOCH_3$ and —$OCH_2CH_2CH_2SO_3H$, when E is benzyloxy, methoxy, propoxy, hexyloxy, heptyloxy, octyloxy or cyclohexyloxy, $R_x$ is selected from the group consisting of
—$NH_2^+CH_2CH_2OH$ $Cl^-$, —$NH_3^{+-}OAc$, =NOH, —$NHCH(CH_3)COO^-K^+$, —$NHCH_2CH_2N(CH_3)_2^{+-}OAc$, —$NHCH_2CH_2SO_3^-K^+$, —$NHCH(COO^-K^+)CH_2CH_2SCH_3$, —$NHCH_2COO^-K^+$, —$OCH(CH_3)COO^-K^+$, —$OCH_2CH_2N(CH_3)_2^{+-}OAc$, —$OCH_2CH_2SO_3^-K^+$, —$OCH(COO^-K^+)CH_2CH_2SCH_3$ and —$OCH_2COO^-K^+$, and

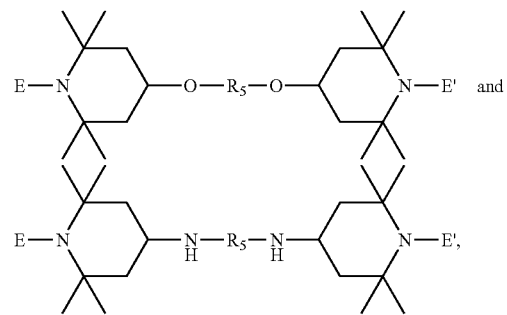

where E and E' are 2-hydroxycyclohexyloxy, 2-hydroxy-2-methylpropoxy, benzyloxy, methoxy, propoxy, hexyloxy, heptyloxy, octyloxy or cyclohexyloxy, and where $R_5$ comprises repeating units selected from the group consisting of
—$(OCH_2CH_2)$—, —$(OCH_2CH(CH_3))$—, —$(CH_2CHCOOH)$—, —$(CH_2C(CH_3)COOH)$—, —$(CH_2CHCOOCH_3)$—, —$(NHCH_2CH_2)$—, —$(CH_2CHOH)$—, —$(CH_2CHCONH_2)$— and —$(CH_2CH(NHCOH))$—.

The following Examples more particularly point out the aspects of the present invention.

The Examples are as follows:

Compounds: Examples 1-18, 22, 37, 39, 43, 52-54, 57, 59-60, 62 and 102-111.

Ink Jet Media: Examples 23, 29-36 and 38.

Solubility: Examples 44-47.

Shampoo Formulations Examples 48-49.

Mouthwash Formulations Examples 50-51.

Coatings: Examples 101, 112-115.

Inks: Examples 19-20 and 24.

Further Ink Jet Media: Examples 21, 25-28 and 40-42.

Further Compounds: Examples 55-56, 58 and 61.

Further Shampoo Formulations: Examples 63-69 and 72.

Body care products, household products, textile and fabrics: Examples 70-71 and 73-76.

Polymer Formulations (compositions, fibers, plaques, combination with flame retardants, etc.): Examples 77-99, 120-125, 144-146, 149-167 and 173-174.

Further Coatings: Examples 100, 116-119, 126-141 and 147-148.

Photographic Compositions: Examples 142-143.

Photocured Inks: Examples 168-169.

Photocured Coatings: Examples 170-172.

EXAMPLE 1

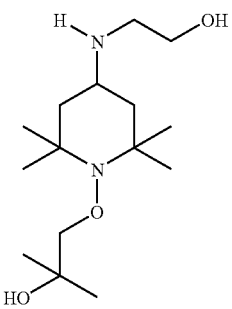

Example 39 (8.4 g, 0.035 mole), ethanolamine (3 g, 0.05 mole), and catalyst (10% Pd on C, 2 g, Engelhard Corp.) are added to 10 mL of isopropanol in 100 mL of ethanol. The reactor is pressured to 45 psig with hydrogen while heating to 60 C. After a reaction time of two hours, the reactor is vented and catalyst is removed by filtration. The solvent is distilled off and the crude product is crystallized from 50 mL of ethyl acetate. The title compound is obtained (5.23 g, 52% yield) as clear white plates with a melting point of 130-132 C whose structure is consistent with HNMR.

EXAMPLE 2

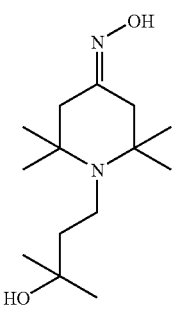

Example 39 (3.36 g, 0.14 mole) and hydroxylamine hydrochloride (1.39 g, 0.02 mole) are dissolved in a solution of 50 mL of water and 50 mL of ethanol. The solution is neutralized to pH=10 with 2N aqueous sodium hydroxide solution. The solution is refluxed for 5 hours after which the solvent is distilled off and the residue is crystallized from ethyl acetate. After drying to constant weight, the title compound is obtained (3.11 g, 86% yield) as a white solid with a melting point of 131-134 C whose structure is consistent with HNMR.

EXAMPLE 3

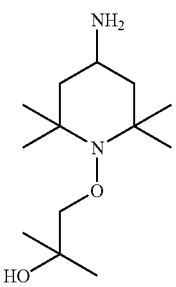

Example 2 (2.44 g, 0.0094 mole) is added to 50 mL of absolute ethanol. Sodium spheres (4 g, 0.17 mole) are added portionwise over thirty minutes after which the mixture is refluxed for one hour. The solution is poured into 200 mL of water and extracted thrice with 100 mL of methylene chloride. The combined organic layer is washed twice with 25 mL of water, dried over magnesium sulfate, and the solvent is distilled off. The title compound is obtained (2.3 g, 100% yield) as a white solid with a melting point of 110-114 C whose structure is consistent with HNMR.

EXAMPLE 4

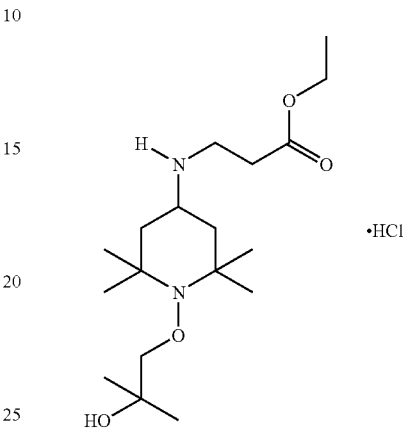

Example 39 (5.28 g, 0.022 mole), beta-alanine ethylester hydrochloride (3.84 G, 0.025 mole), and catalyst (PtO$_2$, 1.0 g, Engelhard Corp.) are added to 75 mL of absolute ethanol. The reactor is pressured up to 45 psig with hydrogen while heating to 60 C. After four hours, the reactor is vented and the catalyst is removed by filtration. Sixty-five mL of ethanol was distilled yielding a precipitate in the remaining ethanol. After filtration, the precipitate is recrystallized from methanol. The title compound is obtained as a white solid with a melting point of 215-220 C whose structure is consistent with HNMR.

EXAMPLE 5

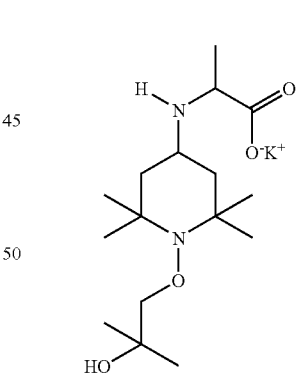

Example 39 (5.28 g, 0.022 mole), 1-alanine (2.23 g, 0.025 mole), potassium hydroxide (1.4 g, 0.025 mole), and catalyst (PtO$_2$, 0.5 g, Engelhard Corp.) are added to 50 mL of absolute methanol. The reactor is pressured up to 45 psig with hydrogen while heating to 60 C. After four hours, the reactor is vented and the catalyst is removed by filtration. The solvent is removed by distillation and the residue is dried in vacuo, which crystallizes during drying. The title compound is obtained (7 g, 100% yield) as a white glassy solid with a melting point of 65-70 C whose structure is consistent with HNMR.

EXAMPLE 6

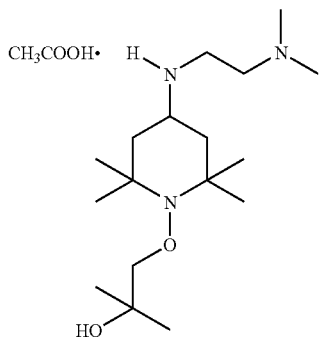

Example 39 (5.28 g, 0.022 mole), N,N-ethylenediamine (2.2 g, 0.025 mole), and catalyst (PtO$_2$, 0.5 g, Engelhard Corp.) are added to 75 mL of absolute methanol. The reactor is pressured up to 45 psig with hydrogen while heating to 60 C. After one hour, the reactor is vented and the catalyst is removed by filtration. The solvent is removed by distillation and the residue is dissolved in 10 mL of acetonitrile and titrated with 1.5 g of glacial acetic acid. The solvent is removed by distillation and the residue is dried overnight in a vacuum oven. The title compound is obtained (7.69 g) as a white solid with a melting point of 72-74 C whose structure is consistent with HNMR.

EXAMPLE 7

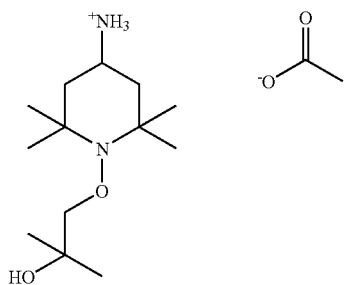

Example 3 (2.55 g, 0.01 mole) is dissolved in 100 mL of diethylether. To this solution is added 0.56 g of glacial acetic acid. A solid, which forms immediately, is filtered off, washed with diethylether, and dried to constant weight in a vacuum oven. The title compound is obtained (1.7 g, 56% yield) as a white solid with a melting point of 200-202 C whose structure is consistent with HNMR.

EXAMPLE 8

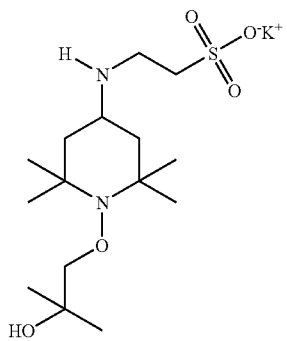

Example 39 (5.28 g, 0.022 mole), taurine (3.12 g, 0.025 mole), and catalyst (PtO$_2$, 0.5 g, Engelhard Corp.) are added to 50 mL of methanol and 25 mL of 1 M methanolic potassium hydroxide. The reactor is pressured to 45 psig with hydrogen while heating to 60 C. After 4 hours, the reactor is vented and the catalyst is filtered off. The filtrate is subjected to vacuum distillation yielding a clear residue that solidifies upon standing. The title compound is obtained (7.7 g, 89.5% yield) as a glassy white solid with a melting point of 158-162 C whose structure is consistent with HNMR.

EXAMPLE 9

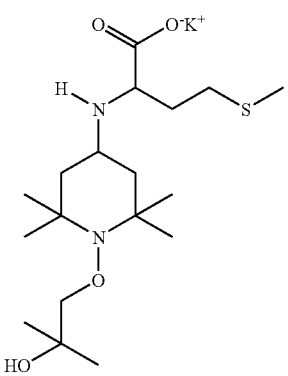

Example 39 (5.28 g, 0.022 mole), methionine (3.72 g, 0.025 mole), and catalyst (PtO$_2$, 0.5 g, Engelhard Corp.) are added to 50 mL of methanol and 25 mL of 1 M methanolic potassium hydroxide. The reactor is pressured to 45 psig with hydrogen while heating to 60 C. After 3 hours, the reactor is vented and the catalyst is filtered off. The filtrate is subjected to vacuum distillation yielding a clear residue that solidifies upon standing. The title compound is obtained (9.45 g) as a white solid with a melting point of 108-112 C whose structure is consistent with HNMR.

EXAMPLE 10

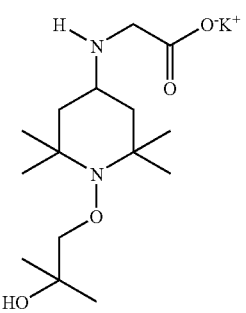

Example 39 (5.28 g, 0.022 mole), glycine (1.88 g, 0.025 mole), and catalyst (PtO$_2$, 0.5 g, Engelhard Corp.) are added to 50 mL of methanol and 25 mL of 1 M methanolic potassium hydroxide. The reactor is pressured to 45 psig with hydrogen while heating to 60 C. After 2 hours, the reactor is vented and the catalyst is filtered off. The filtrate is subjected to vacuum distillation yielding a clear residue that solidifies upon standing. The title compound is obtained (7.87 g) as a white solid with a melting point of 94-98C whose structure is consistent with HNMR.

EXAMPLE 11

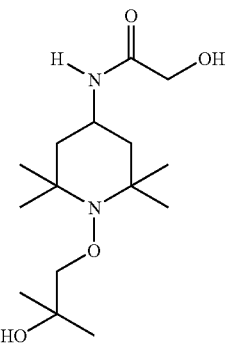

Example 3 (6.11 g, 0.025 mole) and methyl glycolate (4.5 g, 0.05 mole) are added to 75 mL of xylene. Under a nitrogen atmosphere, the solution is heated to 120 C. and held there for 18 hours. The solvent is removed by distillation and the residue is chromatographed on silica gel using a hexane:ethyl acetate gradient. The appropriate fractions are combined and the solvent is removed by distillation yielding a clear residue that solidifies upon standing. The title compound is obtained (1.51 g, 20% yield) as a white solid with a melting point of 153-154 C whose structure is consistent with HNMR.

EXAMPLE 12

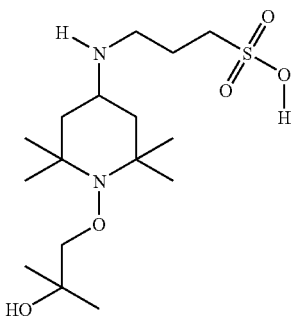

Synthetic Reference: I. Ismail, *J. Serb. Chem. Soc.* 57(7), 415-420 (1992)

Example 3 (4.88 g, 0.02 mole) and 1,1-propanesultone (2.44 g, 0.02 mole) are added to 60 mL of 2-butanol. Under a nitrogen atmosphere, the solution is heated to reflux for 30 minutes. The precipitate is filtered at ambient temperature, washed with 2-butanol, and dried to constant weight in a vacuum oven. The title compound is obtained (4.45 g, 60.5% yield) as a white solid that decomposes upon melting at 290 C whose structure is consistent with HNMR.

EXAMPLE 13

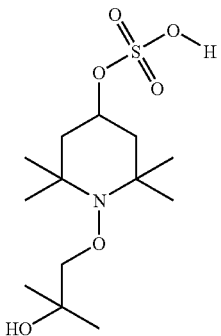

4-Hydroxy-1-(2-hydroxy-2-methylpropoxy)-2,2,6,6-tetramethylpiperidine (4.9 g, 0.02 mole) is dissolved in 200 mL of 1,2-dichloroethane and cooled to 5 C. To this solution is added drop wise chlorosulfonic acid (1.32 mL, 0.02 mole) dissolved in 25 mL of 1,2-dichloroethane. The solution is left stirring overnight allowing the temperature to rise to ambient temperature. The solvent is removed by distillation and replaced with ethanol. The solution is clarified and the ethanol is removed by distillation. The title compound is obtained as a viscous clear resin whose structure is consistent with HNMR.

Analysis:
HNMR (CD$_3$OD): δ 1.29 (s, 6H), 1.56 (s, 6H), 1.57 (s, 6H), 1.82 (dd, 2H), 2.16 (ddd, 2H), 4.16 (tt, 1H), 4.17 (s, 2H)

EXAMPLE 14

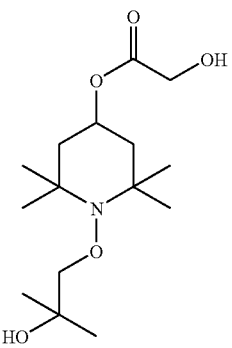

4-Hydroxy-1-(2-hydroxy-2-methylpropoxy)-2,2,6,6-tetramethylpiperidine (12.25 g, 0.05 mole), methyl glycolate (6.75 g, 0.075 mole), and Tyzor TBT (0.5 mL, 0.0013 mole) are dissolved in 250 mL of dry toluene. The solution is heated to reflux and allowed to reflux for 5 hours. The solution is cooled to 100 C at which time 5 mL of water is added. The water is removed, the toluene layer is clarified, and the toluene is removed by distillation. The title compound is obtained (17.56 g) as a light orange oil with an assay of 87% as judged by gas chromatography whose structure is consistent with HNMR.

EXAMPLE 15

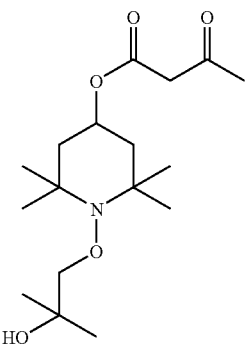

4-Hydroxy-1-(2-hydroxy-2-methylpropoxy)-2,2,6,6-tetramethylpiperidine (12.25 g, 0.05 mole), ethylacetoacetate (7.65 mL, 0.06 mole), and lithium t-butoxide (0.5 g, 0.006 mole) are dissolved in 250 mL of dry toluene. The solution is heated to reflux using a Dean Stark trap and allowed to reflux for 6 hours. The solution is cooled to 100 C at which time 5 mL of water is added to destroy the catalyst. The water is removed, the toluene layer is clarified, and the toluene is removed by distillation. The title compound is obtained (16.7 g) as a light orange oil whose structure is consistent with HNMR.

EXAMPLE 16

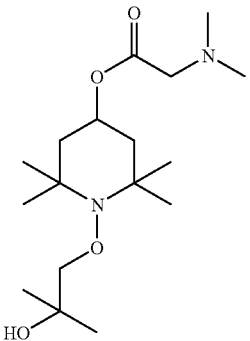

4-Hydroxy-1-(2-hydroxy-2-methylpropoxy)-2,2,6,6-tetramethylpiperidine (12.25 g, 0.05 mole), N,N-dimethylglycine ethyl ester (13 mL, 0.09 mole), and lithium t-butoxide (0.2 g, 0.0025 mole) are dissolved in 150 mL of dry toluene. The solution is heated to reflux using a Dean Stark trap and allowed to reflux for 5 hours. The solution is cooled to 100 C at which time 5 mL of water is added to destroy the catalyst. The water is removed, the toluene layer is clarified, and the toluene is removed by distillation. The title compound is obtained (15.58 g, 94% yield) as a light yellow-orange oil with an assay of 93.2% as judged by gas chromatography whose structure is consistent with HNMR.

EXAMPLE 17

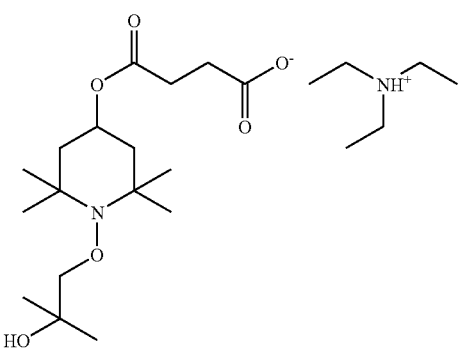

4-Hydroxy-1-(2-hydroxy-2-methylpropoxy)-2,2,6,6-tetramethylpiperidine (12.25 g, 0.05 mole), succinic acid monomethylester (6.6 g, 0.05 mole), triethylamine (5.05 g, 0.05 mole), and lithium t-butoxide (0.4 g, 0.005 mole) are dissolved in 200 mL of dry toluene. The solution is heated to reflux using a Dean Stark trap and allowed to reflux for 8 hours. The solution is cooled to 100 C at which time 5 mL of water is added to destroy the catalyst. The water is removed, the toluene layer is clarified, and the toluene is removed by distillation. The title compound is obtained as a light yellow-orange oil (21.9 g) with an assay of 21% (remaining material is unreacted starting hindered amine) as judged by gas chromatography whose structure is consistent with HNMR.

EXAMPLE 18

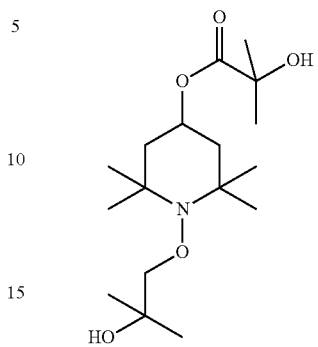

4-Hydroxy-1-(2-hydroxy-2-methylpropoxy)-2,2,6,6-tetramethylpiperidine (12.25 g, 0.05 mole), methyl 4-hydroxyisobutyrate (7.08 g, 0.06 mole), and titanium isopropoxide (0.75 mL, 0.0025 mole) are dissolved in 250 mL of dry toluene. The solution is heated to reflux using a Dean Stark trap and allowed to reflux for 18 hours. The solution is cooled to 100 C at which time 5 mL of water is added to destroy the catalyst. The water is removed, the toluene layer is clarified, and the toluene is removed by distillation. The title compound is obtained (21.41 g) as a light-yellow oil with an assay of 79% as judged by gas chromatography whose structure is consistent with HNMR.

EXAMPLE 19

Ink Jet Ink

An ink-jet ink is prepared by dissolving 2 g of dye in 20 g of diethylene glycol and 78 g of deionized water. The dye used is Acid red 52. The stabilizer is weighed in an amount of 0.15 g into a test tube and dissolved in 2.85 g of ink. The obtained ink is filtered and transferred into an emptied and carefully cleaned cartridge of a Deskjet 510 printer (Hewlett-Packard). A stepped image is then printed onto plain paper (sihl+eika). The produced print is left to dry at 50° C. under vacuum for two hours and thereafter irradiated behind a 5 mm thick window glass in an Atlas Ci-35 light fading device equipped with a Xenon lamp. The Atlas device is operated at 43° C., 50% RH without dark cycles and the light intensity is 461 W/m$^2$ (300-800 nm). The color density of each step is measured before and after exposure using a MacBeth TR 924 densitometer. The compounds according to this invention are able to improve substantially the light fastness of the ink-jet print.

EXAMPLE 20

Magenta and Yellow inks are extracted from an Hewlett-Packard three-color cartridge (HP C1823D). The stabilizer is weighed in an amount of 0.15 g into a test tube and dissolved in 2.85 g of either the magenta or yellow ink. The obtained ink is filtered and transferred into an emptied and carefully cleaned cartridge of a Deskjet 510 printer (Hewlett-Packard). A stepped image is then printed onto plain paper (sihl+eika) or, alternatively, onto Premium Photo paper from Hewlett-Packard (item code C6040A). The produced print is left to dry at 50° C. under vacuum for two hours and thereafter irradiated behind a 5 mm thick window glass in an Atlas Ci-35 light fading device equipped with a Xenon lamp. The Atlas device is operated at 43° C., 50% RH without dark cycles and the light intensity is 461 W/m$^2$ (300-800 nm). The color density of each step is measured before and after exposure using a MacBeth TR 924 densitometer. The compounds according to this invention are able to improve the light fastness of the magenta and yellow prints.

EXAMPLE 21

Ink Jet Media

Canon PR-101 sheets (Canon Japan) are post-treated by casting stabilizer solutions, either aqueous or methanol, using a 75 micron wire wound coating bar. After drying at room temperature, the thus modified sheets are printed with cyan step images using a Canon BJC 8200 printer. The cyan dye used is C.I. Direct Blue 199. The obtained prints are left to dry at 50 C under vacuum for two hours and thereafter are subjected to forced airflow during four weeks. The color density is measured before and after exposure using a MacBeth TR 924 densitometer. The compounds according to this invention are able to improve the light fastness of dyes when printed onto printing media.

EXAMPLE 22

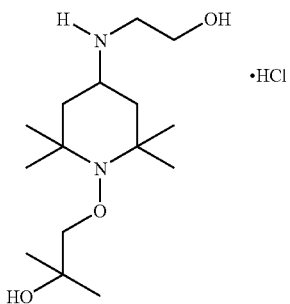

Example 1 (12.02 g as crude product, 0.042 mole) is dissolved in a mixture of diethylether and ethanol. With vigorous agitation, hydrochloric acid gas is introduced subsurface to the solution. A white insoluble solid is formed which is filtered off and dried in a vacuum oven until constant weight is reached. The title compound is obtained (2.16 g, 16% yield) as a white solid with a melting point of 217-233C whose structure is consistent with HNMR.

EXAMPLE 23

Ink Jet Media

A resin-coated paper impregnated with inorganic adsorbent particles (Konica QP Photoglossy ink jet paper, Konica Corp.) is purchased. On the ink-receiving layer, a 0.8 wt % methanol solution, unless stated otherwise, of the instant compounds is applied in an amount to achieve 650-700 mg/m². The paper is allowed to dry under ambient temperature and pressure for 24 hours. Separately, test patterns (cyan) are printed on the treated sheets using a Hewlett Packard DeskJet 970 Cxi printer at 100% print density. The obtained prints are left to dry at ambient temperature and pressure for 24 hours. Color densities and CIEL*a*b coordinates before and after exposure are measured using X-Rite 938 Spectrodensitometer. Exposures are carried out using normal office fluorescent lighting. The change in color is given by Delta E (DE) which is calculated by:

$$DE=[(DL^*)^2+(Da^*)^2+(Db^*)^2]^{1/2}$$

| Stabilizer | DE for cyan after 15 weeks |
| --- | --- |
| None | 4.29 |
| Example 11/DABCO•HCl | 4.08 |
| Example 6/DABCO | 3.09 |

DABCO•HCl is 1,4-diazabicyclo[2.2.2]octane hydrochloride salt.
DABCO is 1,4-diazabicyclo[2.2.2]octane.
Mixtures of stabilizers are in a 1:1 by weight ratio with the total stabilizer concentration added of 650-700 mg/m2.

As the above data show, compounds according to this invention improve the light fastness of ink jet prints.

EXAMPLE 24

The instant compounds are added to an ink composition, for example as disclosed in U.S. Pat. No. 5,855,655 or 5,782,963, at a concentration of 2 wt % and 0.5 wt % respectively. The images printed from these stabilized inks show reduced dye fading and better image permanence.

EXAMPLE 25

A commercial white polyethylene terephthalate sheet is coated with silica and polyvinylalcohol according to U.S. Pat. No. 6,391,440 Example 1. A methanol solution of the instant compounds is applied to this sheet in an amount equivalent to 400 mg/m². The image printed on this receiving layer shows reduced dye fading and better image permanence.

EXAMPLE 26

A commercial white polyethylene terephthalate sheet is coated with alumina hydrate and polyvinylalcohol according to U.S. Pat. No. 6,391,440 Example 5. A methanol solution of the instant compounds is applied to this sheet in an amount equivalent to 400 mg/m². The image printed on this receiving layer shows reduced dye fading and better image permanence.

EXAMPLE 27

A paper sheet containing alumina is prepared according to U.S. Pat. No. 6,391,440 Example 8. A methanol solution of the instant compounds is applied to this sheet in an amount equivalent to 600 mg/m2. The image printed on this receiving layer shows reduced dye fading and better image permanence.

EXAMPLE 28

A paper sheet containing silica is prepared according to U.S. Pat. No. 5,165,973. A methanol solution of the instant compounds is applied to this sheet in an amount equivalent to 700 mg/m2. The image printed on this receiving layer shows reduced dye fading and better image permanence.

EXAMPLE 29

A resin-coated paper impregnated with inorganic adsorbent particles (Konica QP Photoglossy ink jet paper, Konica Corp.) is purchased. On the ink-receiving layer, a 0.8 wt % methanol solution of the instant compounds is applied in an amount to achieve 650-700 mg/m². The paper is allowed to dry under ambient temperature and pressure for 24 hours. Separately, test patterns (magenta) are printed on the treated sheets using a Hewlett Packard DeskJet 970 Cxi printer at 100% print density. The obtained prints are left to dry at ambient temperature and pressure for 24 hours. Color densities and CIEL*a*b coordinates before and after exposure are measured using X-Rite 938 Spectrodensitometer. Exposures are carried out using normal office fluorescent lighting.

| Stabilizer | DE for magenta after 15 weeks |
|---|---|
| None | 5.49 |
| Example 11/DABCO•HCl | 4.79 |
| Example 6/DABCO | 2.23 |

DABCO•HCl is 1,4-diazabicyclo[2.2.2]octane hydrochloride salt.
DABCO is 1,4-diazabicyclo[2.2.2]octane.
Mixtures of stabilizers are in a 1:1 by weight ratio with the total stabilizer concentration added of 650-700 mg/m2.

As the above data show, compounds according to this invention improve the light fastness of ink jet prints.

EXAMPLE 30

A resin-coated paper impregnated with inorganic adsorbent particles (Konica QP Photoglossy ink jet paper, Konica Corp.) is purchased. On the ink-receiving layer, a 0.8 wt % methanol solution of the instant compounds is applied in an amount to achieve 650-700 mg/m$^2$. The paper is allowed to dry under ambient temperature and pressure for 24 hours. Separately, test patterns (yellow) are printed on the treated sheets using a Hewlett Packard DeskJet 970 Cxi printer at 100% print density. The obtained prints are left to dry at ambient temperature and pressure for 24 hours. Color densities and CIEL*a*b coordinates before and after exposure are measured using X-Rite 938 Spectrodensitometer. Exposures are carried out using normal office fluorescent lighting.

| Stabilizer | DE for yellow after 15 weeks |
|---|---|
| None | 2.48 |
| Example 11/DABCO•HCl | 2.35 |
| Example 6/DABCO | 1.73 |

DABCO•HCl is 1,4-diazabicyclo[2.2.2]octane hydrochloride salt.
DABCO is 1,4-diazabicyclo[2.2.2]octane.
Mixtures of stabilizers are in a 1:1 by weight ratio with the total stabilizer concentration added of 650-700 mg/m2.

As the above data show, compounds according to this invention improve the light fastness of ink jet prints.

EXAMPLE 31

A resin-coated paper impregnated with inorganic adsorbent particles (Konica QP Photoglossy ink jet paper, Konica Corp.) is purchased. On the ink-receiving layer, a 0.8 wt % methanol solution of the instant compounds is applied in an amount to achieve 650-700 mg/m$^2$, unless otherwise stated. The paper is allowed to dry under ambient temperature and pressure for 24 hours. Separately, test patterns (cyan) are printed on the treated sheets using a Hewlett Packard DeskJet 970 Cxi printer at 100% print density. The obtained prints are left to dry at ambient temperature and pressure for 24 hours. Color densities and CIEL*a*b coordinates before and after exposure are measured using X-Rite 938 Spectrodensitometer. Exposures are carried out using normal office fluorescent lighting.

| Stabillizer | DE for cyan after 4 weeks |
|---|---|
| None | 6.19 |
| Example 22 | 5.26 |
| Example 2 | 4.69 |
| Example 22 (2x) | 4.62 |
| Example 7 | 4.27 |
| Example 1 | 4.21 |

Example 22 (2x) is done at a concentration of 1300 to 1400 mg/m2.

As the above data show, compounds according to this invention improve the light fastness of ink jet prints.

EXAMPLE 32

A resin-coated paper impregnated with inorganic adsorbent particles (Konica QP Photoglossy ink jet paper, Konica Corp.) is purchased. On the ink-receiving layer, a 0.8 wt % methanol solution of the instant compounds is applied in an amount to achieve 650-700 mg/m$^2$, unless otherwise stated. The paper is allowed to dry under ambient temperature and pressure for 24 hours. Separately, test patterns (magenta) are printed on the treated sheets using a Hewlett Packard DeskJet 970 Cxi printer at 100% print density. The obtained prints are left to dry at ambient temperature and pressure for 24 hours. Color densities and CIEL*a*b coordinates before and after exposure are measured using X-Rite 938 Spectrodensitometer. Exposures are carried out using normal office fluorescent lighting.

| Stabilizer | DE for magenta after 4 weeks |
|---|---|
| None | 25.73 |
| Example 22 | 25.20 |
| Example 22 (2x) | 21.96 |
| Example 7 | 20.78 |
| Example 1 | 20.23 |
| Example 7 (2x) | 19.52 |
| Example 7 (3x) | 12.99 |

Example 22 (2x) and Example 7 (2x) are done at a concentration of 1300 to 1400 mg/m2 while Example 7 (3x) is done at a concentration of 1950 to 2100 mg/m2.

As the above data show, compounds according to this invention improve the light fastness of ink jet prints.

EXAMPLE 33

A resin-coated paper impregnated with inorganic adsorbent particles (Konica QP Photoglossy ink jet paper, Konica Corp.) is purchased. On the ink-receiving layer, a 0.8 wt % methanol solution of the instant compounds is applied in an amount to achieve 650-700 mg/m$^2$, unless stated otherwise. The paper is allowed to dry under ambient temperature and pressure for 24 hours. Separately, test patterns (yellow) are printed on the treated sheets using a Hewlett Packard DeskJet 970 Cxi printer at 50% print density. The obtained prints are left to dry at ambient temperature and pressure for 24 hours. Color densities and CIEL*a*b coordinates before and after exposure are measured using X-Rite 938 Spectrodensitometer. Exposures are carried out using normal office fluorescent lighting.

| Stabilizer | DE for yellow after 4 weeks |
|---|---|
| None | 5.80 |
| Example 22 | 5.53 |
| Example 2 | 3.87 |

As the above data show, compounds according to this invention improve the light fastness of ink jet prints.

EXAMPLE 34

A resin-coated paper impregnated with inorganic adsorbent particles (Konica QP Photoglossy ink jet paper, Konica Corp.) is purchased. On the ink-receiving layer, a 0.8 wt % methanol solution of the instant compounds is applied in an amount to achieve 650-700 mg/m$^2$, unless otherwise stated. The paper is allowed to dry under ambient temperature and pressure for 24 hours. Separately, test patterns (cyan) are printed on the treated sheets using a Hewlett Packard DeskJet 970 Cxi printer at 50% print density. The obtained prints are left to dry at ambient temperature and pressure for 24 hours. Color densities and CIEL*a*b coordinates before and after exposure are measured using X-Rite 938 Spectrodensitometer. Exposures are carried out using normal office fluorescent lighting.

| Stabilizer | DE for cyan after 4 weeks |
| --- | --- |
| None | 7.29 |
| Example 22 | 5.98 |
| Example 7 | 5.85 |
| Example 2 | 5.53 |
| Example 1 | 5.29 |
| Example 22 (2x) | 5.11 |
| Example 7 (2x) | 4.95 |
| Example 7 (3x) | 4.34 |

Example 22 (2x) and Example 7 (2x) are done at a concentration of 1300 to 1400 mg/m2 while Example 7 (3x) is done at a concentration of 1950 to 2100 mg/m2.

As the above data show, compounds according to this invention improve the light fastness of ink jet prints.

EXAMPLE 35

A resin-coated paper impregnated with inorganic adsorbent particles (Konica QP Photoglossy ink jet paper, Konica Corp.) is purchased. On the ink-receiving layer, a 0.8 wt % methanol solution of the instant compounds is applied in an amount to achieve 650-700 mg/m$^2$, unless otherwise stated. The paper is allowed to dry under ambient temperature and pressure for 24 hours. Separately, test patterns (magenta) are printed on the treated sheets using a Hewlett Packard DeskJet 970 Cxi printer at 50% print density. The obtained prints are left to dry at ambient temperature and pressure for 24 hours. Color densities and CIEL*a*b coordinates before and after exposure are measured using X-Rite 938 Spectrodensitometer. Exposures are carried out using normal office fluorescent lighting.

| Stabilizer | DE for magenta after 4 weeks |
| --- | --- |
| None | 20.16 |
| Example 7 | 16.62 |
| Example 7 (2x) | 14.14 |
| Example 7 (3x) | 8.60 |

Example 7 (2x) is done at a concentration of 1300 to 1400 mg/m2 while Example 7 (3x) is done at a concentration of 1950 to 2100 mg/m2.

As the above data show, compounds according to this invention improve the light fastness of ink jet prints.

EXAMPLE 36

A resin-coated paper impregnated with inorganic adsorbent particles (Konica QP Photoglossy ink jet paper, Konica Corp.) is purchased. On the ink-receiving layer, a 0.8 wt % methanol solution of the instant compounds is applied in an amount to achieve 650-700 mg/m$^2$, unless stated otherwise. The paper is allowed to dry under ambient temperature and pressure for 24 hours. Separately, test patterns (yellow) are printed on the treated sheets using a Hewlett Packard DeskJet 970 Cxi printer at 50% print density. The obtained prints are left to dry at ambient temperature and pressure for 24 hours. Color densities and CIEL*a*b coordinates before and after exposure are measured using X-Rite 938 Spectrodensitometer. Exposures are carried out using normal office fluorescent lighting.

| Stabilizer | DE for yellow after 4 weeks |
| --- | --- |
| None | 4.68 |
| Example 22 | 3.15 |
| Example 2 | 1.36 |

As the above data show, compounds according to this invention improve the light fastness of ink jet prints.

EXAMPLE 37

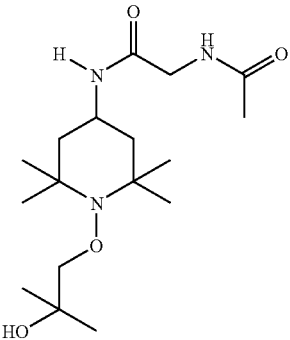

Example 3 (6.1 g, 0.025 mole) and ethyl acetamidoacetate (3.62 g, 0.025 mole) are added to 75 mL of xylene and heated to reflux. The solution is refluxed for 18 hours and then the xylene is removed by distillation. The remaining orange residue is recrystallized from methylene chloride and dried to constant weight in a vacuum oven. The title compound is obtained (2.41 g, 28% yield) as a white crystalline solid with a melting point of 77-80C whose structure is consistent with HNMR.

EXAMPLE 38

A resin-coated paper impregnated with inorganic adsorbent particles (Konica QP Photoglossy ink jet paper, Konica Corp.) is purchased. On the ink-receiving layer, a 0.8 wt % methanol solution of the instant compounds is applied in an amount to achieve 650-700 mg/m$^2$. The paper is allowed to dry under ambient temperature and pressure for 24 hours. Separately, test patterns (cyan and yellow) are printed on the treated sheets using a Hewlett Packard DeskJet 970 Cxi printer at 100% print density. The obtained prints are left to dry at ambient temperature and pressure for 24 hours. Color densities and CIEL*a*b coordinates before and after exposure are measured using X-Rite 938 Spectrodensitometer. Exposures are carried out using normal office fluorescent lighting.

| Stabilizer | DE for cyan after 3 months |
|---|---|
| None | 12.40 |
| Compound A | 11.96 |
| Example 37 | 11.39 |
| Compound A/Example 37 | 10.96 |

Compound A is N,N-dibenzylhydroxylamine hydrochloride

Mixtures of stabilizers are in a 1:1 by weight ratio with the total stabilizer concentration added of 650-700 mg/m2.

| Stabilizer | DE for yellow after 3 months |
|---|---|
| None | 6.85 |
| Compound A | 5.31 |
| Example 37 | 2.96 |
| Example 37/Compound A | 1.37 |

Compound A is N,N-dibenzylhydroxylamine hydrochloride

Mixtures of stabilizers are in a 1:1 by weight ratio with the total stabilizer concentration added of 650-700 mg/m2.

As the above data show, compounds according to this invention improve the light fastness of ink jet prints.

EXAMPLE 39

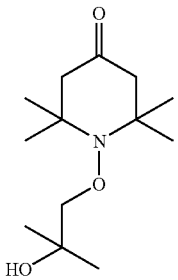

4-Hydroxy-1-(2-hydroxy-2-methylpropoxy)-2,2,6,6-tetramethylpiperidine (42.5 g, 0.17 mole), calcium hypochlorite (100 g, 0.7 mole), and resin (25 g, IRA 900 resin, ACROS) are added to 600 mL of carbon tetrachloride. After heating to 40 C, the slurry is stirred for seven hours and then is stirred overnight at ambient temperature. The slurry is filtered to remove resin and salts. The resulting filtrate is washed twice with water, dried over magnesium sulfate and the solvent removed by distillation. The title compound is obtained (37.1 g, 88% yield) as a white solid with a melting point of 58-61C whose structure is consistent with HNMR.

EXAMPLE 40

Ink Jet Media

A resin-coated paper impregnated with inorganic adsorbent particles (Konica QP Photoglossy ink jet paper, Konica Corp.) is purchased. On the ink-receiving layer, a 0.8 wt % methanol solution of the instant compounds and 2-(2-hydroxy-3-tert-butyl-5-methylphenyl)-2H-benzotriazole-5-sulfonic acid, sodium salt, a benzotriazole based UV absorber, is applied in an amount to achieve 650-700 mg/m². The UV absorber and the instant compounds are in a 2:1 ratio by weight. The paper is allowed to dry under ambient temperature and pressure for 24 hours. Separately, test patterns (cyan, magenta and yellow) are printed on the treated sheets using an Epson printer at 100% print density. The obtained prints are left to dry at ambient temperature and pressure for 24 hours. Color densities and CIEL*a*b coordinates before and after exposure are measured using X-Rite 938 Spectrodensitometer. Exposures are carried out using normal office fluorescent lighting. The compounds according to this invention—improve the light fastness of ink jet prints.

EXAMPLE 41

A resin-coated paper impregnated with inorganic adsorbent particles (Konica QP Photoglossy ink jet paper, Konica Corp.) is purchased. On the ink-receiving layer, a 0.8 wt % methanol solution of the instant compounds and 2-(3-t-butyl-2-hydroxy-5-(2-ω-hydroxy-octa-(ethyleneoxy)carbonyl-ethyl)-, phenyl)-2H-benzotriazole, a benzotriazole based UV absorber, is applied in an amount to achieve 650-700 mg/m². The UV absorber and the instant compounds are in a 1:1 ratio by weight. The paper is allowed to dry under ambient temperature and pressure for 24 hours. Separately, test patterns (cyan, magenta and yellow) are printed on the treated sheets using a Hewlett Packard DeskJet 970 Cxi printer at 50% print density. The obtained prints are left to dry at ambient temperature and pressure for 24 hours. Color densities and CIEL*a*b coordinates before and after exposure are measured using X-Rite 938 Spectrodensitometer. Exposures are carried out using uv lamps. The compounds according to this invention improve the light fastness of ink jet prints.

EXAMPLE 42

A resin-coated paper impregnated with inorganic adsorbent particles (Konica QP Photoglossy ink jet paper, Konica Corp.) is purchased. On the ink-receiving layer, a 0.8 wt % methanol solution of the instant compounds and 2-(2-hydroxy-3-tert-butyl-5-methylphenyl)-2H-benzotriazole-5-sulfonic acid, sodium salt, a benzotriazole based UV absorber, is applied in an amount to achieve 650-700 mg/m². The UV absorber and the instant compounds are in a 1:1 ratio by weight. The paper is allowed to dry under ambient temperature and pressure for 24 hours. Separately, test patterns (cyan, magenta and yellow) are printed on the treated sheets using a Hewlett Packard DeskJet 970 Cxi printer at 100% print density. The obtained prints are left to dry at ambient temperature and pressure for 24 hours. Color densities and CIEL*a*b coordinates before and after exposure are measured using X-Rite 938 Spectrodensitometer. Exposures are carried out using normal office fluorescent lighting. The compounds according to this invention improve the light fastness of ink jet prints.

EXAMPLE 43

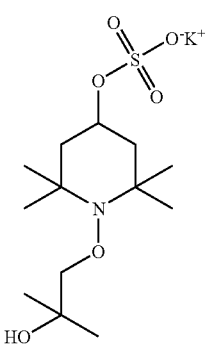

Example 13 (0.304 g, 0.001 mole) is dissolved in 2 mL of absolute ethanol. Potassium hydroxide (0.05 g, 0.001 mole) is added to the solution at which time a precipitate is formed. The precipitate is filtered and dried to constant weight in a vacuum oven. The title compound is obtained as a waxy white solid with a melting point of 115-120C whose structure is consistent with HNMR.

EXAMPLE 44

The solubility of the instant compounds is evaluated in polar solvent systems. A solution of 50% butyl carbitol by weight and 50% water by weight is prepared. The instant compounds are added to this solution, stirred for 30 minutes, and sampled for analysis. Samples containing bis(1-octyloxy-2,2,6,6-tetramethylpiperidin-4-yl) sebacate and 4-hydroxy-1-(2-hydroxy-2-methylpropoxy)-2,2,6,6-tetramethylpiperidine are filtered to remove any undissolved residue and all samples are analyzed by high pressure liquid chromatography or gas chromatography.

| Compound | Solubility (% by weight) |
| --- | --- |
| HALS A | 0.2 |
| HALS B | 13.4 |
| Example 5 | ≧15 |
| Example 10 | ≧20 |

HALS A is bis(1-octyloxy-2,2,6,6-tetramethylpiperidin-4-yl) sebacate;
HALS B is 4-hydroxy-1-(2-hydroxy-2-methylpropoxy)-2,2,6,6-tetramethylpiperidine.

This demonstrates that the instant compounds are soluble in highly polar solvents.

EXAMPLE 45

The solubility of the instant compounds is evaluated in polar solvent systems. A solution of 50% butyl cellusolve by weight and 50% water by weight is prepared. The instant compounds are added to this solution, stirred for 30 minutes, and sampled for analysis. Samples containing bis(1-octyloxy-2,2,6,6-tetramethylpiperidin-4-yl) sebacate and 4-hydroxy-1-(2-hydroxy-2-methylpropoxy)-2,2,6,6-tetramethylpiperidine are filtered to remove any undissolved residue and all samples are analyzed by high pressure liquid chromatography or gas chromatography.

| Compound | Solubility (% by weight) |
| --- | --- |
| HALS A | 0.7 |
| HALS B | 15.5 |
| Example 5 | ≧18 |
| Example 10 | ≧20 |

HALS A is bis(1-octyloxy-2,2,6,6-tetramethylpiperidin-4-yl) sebacate;
HALS B is 4-hydroxy-1-(2-hydroxy-2-methylpropoxy)-2,2,6,6-tetramethylpiperidine.

This demonstrates that the instant compounds are soluble in highly polar solvents.

EXAMPLE 46

The solubility of the instant compounds is evaluated in polar solvent systems. A solution of 25% butyl cellusolve by weight and 75% water by weight is prepared. The instant compounds are added to this solution, stirred for 30 minutes, and sampled for analysis. Samples containing bis(1-octyloxy-2,2,6,6-tetramethylpiperidin-4-yl) sebacate and 4-hydroxy-1-(2-hydroxy-2-methylpropoxy)-2,2,6,6-tetramethylpiperidine are filtered to remove any undissolved residue and all samples are analyzed by high pressure liquid chromatography or gas chromatography.

| Compound | Solubility (% by weight) |
| --- | --- |
| HALS A | <0.1 |
| HALS B | 13.6 |
| Example 10 | ≧18 |

HALS A is bis(1-octyloxy-2,2,6,6-tetramethylpiperidin-4-yl) sebacate.
HALS B is 4-hydroxy-1-(2-hydroxy-2-methylpropoxy)-2,2,6,6-tetramethylpiperidine.

This demonstrates that the instant compounds are soluble in highly polar solvents.

EXAMPLE 47

The solubility of the instant compounds is evaluated in polar solvent systems. The instant compounds are added to water, stirred for 30 minutes, and sampled for analysis. Samples containing bis(1-octyloxy-2,2,6,6-tetramethylpiperidin-4-yl) sebacate and 4-hydroxy-1-(2-hydroxy-2-methylpropoxy)-2,2,6,6-tetramethylpiperidine are filtered to remove any undissolved residue and all samples are analyzed by high pressure liquid chromatography or gas chromatography.

| Compound | Solubility (% by weight) |
| --- | --- |
| HALS A | <0.1 |
| HALS B | 1.4 |
| Example 10 | ≧8 |

HALS A is bis(1-octyloxy-2,2,6,6-tetramethylpiperidin-4-yl) sebacate;
HALS B is 4-hydroxy-1-(2-hydroxy-2-methylpropoxy)-2,2,6,6-tetramethylpiperidine.

This demonstrates that the instant compounds are soluble in highly polar solvents.

EXAMPLE 48

The instant compounds are added to a commercial shampoo formulation and are evaluated for their ability to reduce the amount of dye fading when the samples are exposed to fluorescent lighting. The instant compounds (0.36 g) are dissolved in 5 mL of methanol which is then added to 120 g of shampoo (Suave$^R$ Natural$^R$, Fresh Mountain Strawberry) with agitation. A benzotriazole UV absorber, 2-(2-hydroxy-3-tert-butyl-5-methylphenyl)-2H-benzotriazole-5-sulfonic acid, sodium salt (UVA), is optionally added to the shampoo formulation at an equivalent concentration. The stabilized shampoo formulation is agitated for 15 minutes and put into 20 mL glass scintillation vials. These formulations are weathered under fluorescent light aging at ambient temperature. The CIEL*a*b coordinates before and after exposure are measured using X-Rite 938 Spectrodensitometer. Color change is expressed as Delta E (DE).

| Stabilizer/(Loading) | DE after 2 weeks |
| --- | --- |
| None | 11.74 |
| Example 17/(0.30 wt %) | 8.91 |
| Example 6/(0.30 wt %) | 7.53 |
| Example 6/UVA (0.30 wt %/0.30 wt %) | 2.33 |

The compounds according to this invention improve the light fastness of shampoo formulations.

EXAMPLE 49

The instant compounds are added to a commercial shampoo formulation and are evaluated for their ability to reduce the amount of dye fading when the samples are exposed to fluorescent lighting. The instant compounds (0.36 g) are dissolved in 5 mL of methanol which is then added to 120 g of shampoo (Clairol$^R$ Herbal Essences Shampoo) with agitation. A benzotriazole UV absorber, 2-(2-hydroxy-3-tert-butyl-5-methylphenyl)-2H-benzotriazole-5-sulfonic acid, sodium salt (UVA), is optionally added to the shampoo formulation. The stabilized shampoo formulation is agitated for 15 minutes and put into 20 mL glass scintillation vials. These formulations are weathered under fluorescent light aging at ambient temperature. The CIEL*a*b coordinates before and after exposure are measured using X-Rite 938 Spectrodensitometer. Color change is expressed as Delta E (DE).

| Stabilizer/(Loading) | DE after 2 weeks |
| --- | --- |
| None | 8.87 |
| Example 7/(0.30 wt %) | 3.96 |
| Example 5/(0.30 wt %) | 1.55 |
| Example 7/UVA (0.15 wt %/0.15 wt %) | 0.86 |

The compounds according to this invention improve the light fastness of shampoo formulations.

EXAMPLE 50

The instant compounds are added to a commercial mouthwash formulation and are evaluated for their ability to reduce the amount of dye fading when the samples are exposed to fluorescent lighting. The instant compounds (0.36 g) are dissolved in 5 mL of methanol which is then added to 120 g of mouthwash (Scope$^R$ Original Mint) with agitation. A benzotriazole UV absorber, 2-(2-hydroxy-3-tert-butyl-5-methylphenyl)-2H-benzotriazole-5-sulfonic acid, sodium salt (UVA), is optionally added to the mouthwash formulation. The stabilized mouthwash formulation is agitated for 15 minutes and put into 20 mL glass scintillation vials. These formulations are weathered under fluorescent light aging at ambient temperature. The CIEL*a*b coordinates before and after exposure are measured using X-Rite 938 Spectrodensitometer. Color change is expressed as Delta E (DE).

| Stabilizer/(Loading) | DE after 2 weeks |
| --- | --- |
| None | 6.15 |
| Example 18/(0.30 wt %) | 5.11 |
| Example 8/UVA (0.15 wt %/0.15 wt %) | 4.28 |

The compounds according to this invention improve the light fastness of mouthwash formulations.

EXAMPLE 51

The instant compounds are added to a commercial mouthwash formulation and are evaluated for their ability to reduce the amount of dye fading when the samples are exposed to fluorescent lighting. The instant compounds (0.36 g) are dissolved in 5 mL of methanol which is then added to 120 g of mouthwash (Listerine$^R$ Cool Mint) with agitation. A benzotriazole UV absorber, 2-(2-hydroxy-3-tert-butyl-5-methylphenyl)-2H-benzotriazole-5-sulfonic acid, sodium salt (UVA), is optionally added to the mouthwash formulation. The stabilized mouthwash formulation is agitated for 15 minutes and put into 20 mL glass scintillation vials. These formulations are weathered under fluorescent light aging at ambient temperature. The CIEL*a*b coordinates before and after exposure are measured using X-Rite 938 Spectrodensitometer. Color change is expressed as Delta E (DE).

| Stabilizer/(Loading) | DE after 35 days |
| --- | --- |
| None | 1.83 |
| Example 10/UVA (0.15 wt %/0.15 wt %) | 1.21 |

The compounds according to this invention improve the light fastness of mouthwash formulations.

EXAMPLE 52

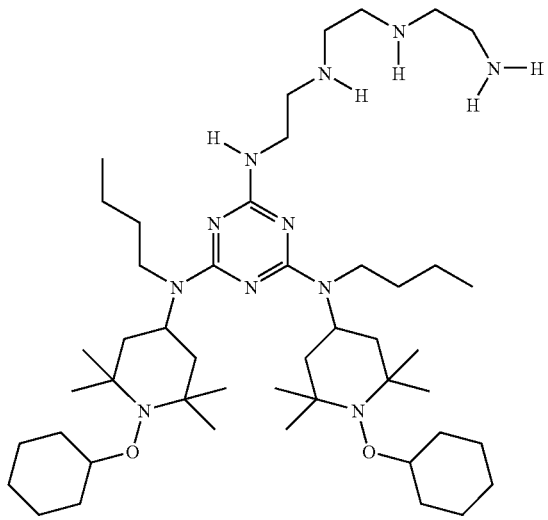

2,4-Bis[(1-cyclohexyloxy-2,2,6,6-tetramethylpiperidin-4-yl)butylamino]-6-chloro-1,3,5-triazine (20 g, 27.8 mmol) is added to DMF (150 g) at 60° C. in a stirred vessel. N4 amine (50.3 g, 288 mmol, BASF) is quickly added and the reaction mass is stirred at 60-65° C. for 1.5 hrs. Cyclohexane (150 mL) and water (200 g) are then added and the reaction mass is stirred at 50-55° C. After 15 minutes, the layers are allowed to separate. The aqueous layer is washed with cyclohexane (70 mL) at 50° C. and the cyclohexane layers are combined. The combined cyclohexane layer is washed thrice with water (100 mL/wash) at 50-55° C. The cyclohexane layer is briefly dried over anhydrous Na$_2$SO$_4$ before removing the solvent under reduced pressure. The title compound is received (24.2 g) as a light yellow oil whose structure is consistent with HNMR.

EXAMPLE 53

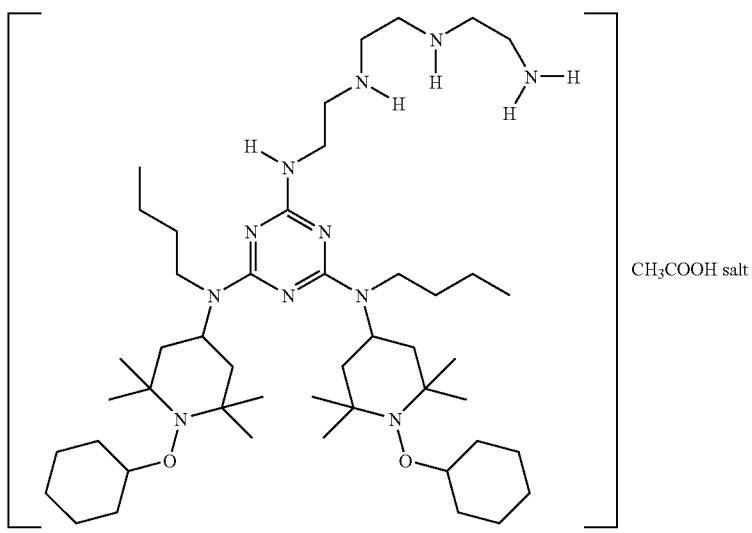

Example 52 (24.2 g, 27.8 mmol) is combined with cyclohexane (70 ml) and glacial acetic acid (1.68 g, 27.8 mmol). The solution is stirred 5 minutes and the solvent stripped under reduced pressure until constant weight. The title compound is received (25 g) as an off white solid whose structure is consistent with HNMR.

EXAMPLE 54

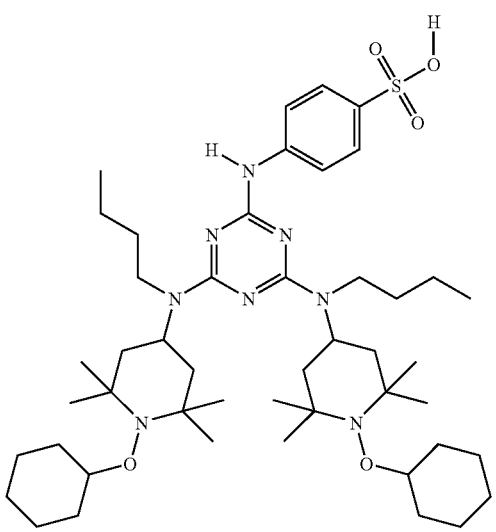

2,4-Bis[(1-cyclohexyloxy-2,2,6,6-tetramethylpiperidin-4-yl)butylamino]-6-chloro-1,3,5-triazine (13.0 g, 0.0178 mole) and N,N-dimethylformamide (12.5 g, 1.71 mole) are added to a 500 mL laboratory flask equipped with the necessary auxiliary equipment. This solution is heated to 100 C. at which time sulfanilic acid (14.9 g, 0.0857 mole) and anhydrous potassium carbonate (11.0 g, 0.0796 mole) are added. The temperature is raised to 145-150C at which time sodium hydroxide (1.24 g, 0.031 mole) is added. After 15 hours at 145-150C, the reaction is cooled, diluted with water, and extracted with hexane. The lower aqueous layer is removed and further washed with hexane. The combined hexane extracts is washed thrice with water at 50 C. The organic solvent is removed and the product is dried until constant weight. The title compound is received (17.1 g) as a yellow glassy solid whose structure is consistent with HNMR.

EXAMPLE 55

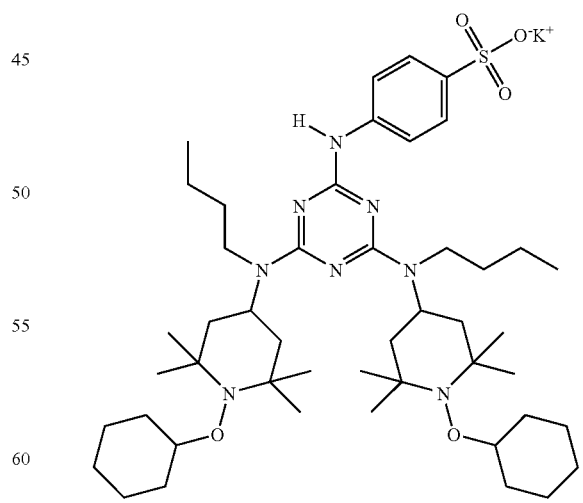

Example 54 is dissolved in 2-propanol and heated to 50 C. The product is titrated with potassium hydroxide. The solvent is removed under vacuum and the resulting title compound is dried to constant weight.

EXAMPLE 56

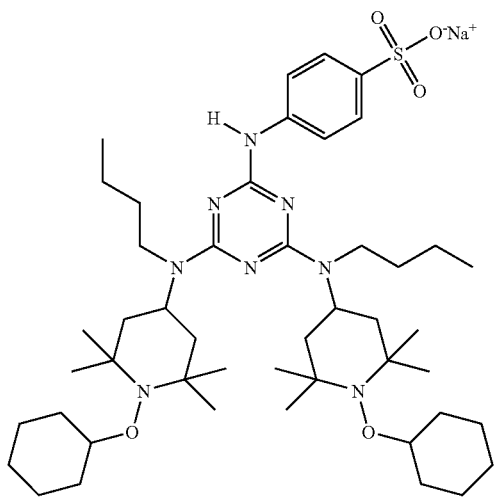

Example 54 is dissolved in 2-propanol and heated to 50 C. The product is titrated with sodium hydroxide. The solvent is removed under vacuum and the resulting title compound is dried to constant weight.

EXAMPLE 57

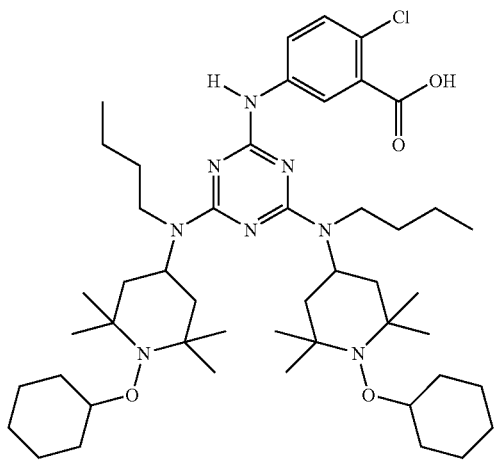

2,4-Bis[(1-cyclohexyloxy-2,2,6,6-tetramethylpiperidin-4-yl)butylamino]-6-chloro-1,3,5-triazine (13.0 g, 0.0178 mole) and N,N-dimethylformamide (12.5 g, 1.71 mole) are added to a 500 mL laboratory flask equipped with the necessary auxiliary equipment. This solution is heated to 85 C at which time 5-amino-2-chlorobenzoic acid (15 g, 0.0874 mole) and anhydrous potassium carbonate (11.0 g, 0.0796 mole) are added. The temperature is raised slowly to 120 C and held at this temperature for 15 hours. The reaction is then diluted with water and extracted with hexane. The lower aqueous layer is removed and further washed with hexane. The combined hexane extracts is washed thrice with water at 50 C. The organic solvent is removed and the product is dried until constant weight. The title compound is received (14.5 g) as a light yellow glassy solid.

EXAMPLE 58

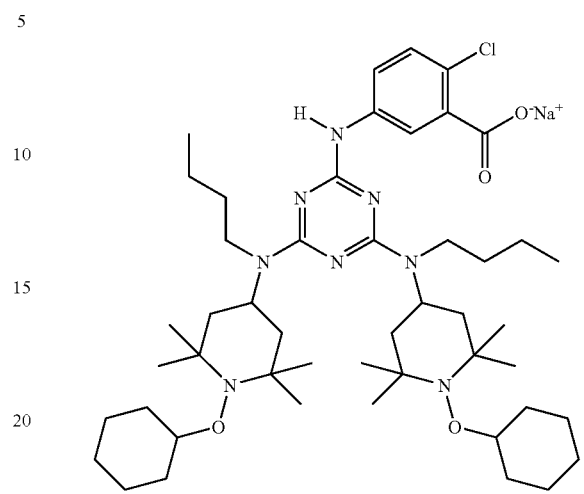

Example 57 is dissolved in 2-propanol and heated to 50 C. The product is titrated with sodium hydroxide. The solvent is removed under vacuum and the resulting title compound is dried to constant weight.

EXAMPLE 59

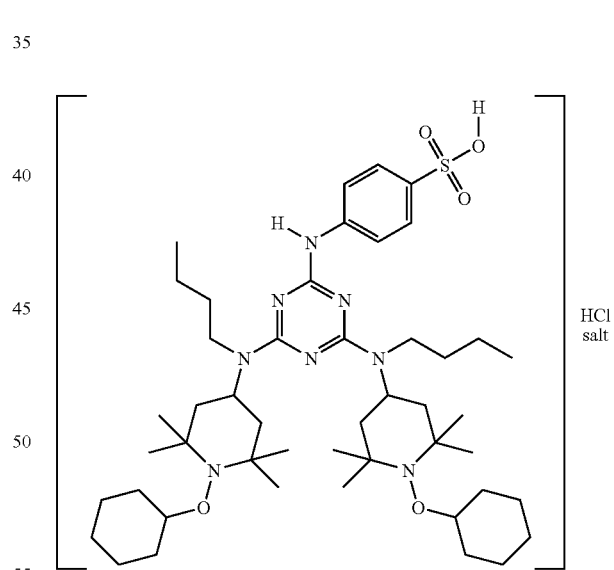

Example 54 (17.1 g, 0.0197 mole) is dissolved in anhydrous 2-propanol (150 g, 2.5 mole) and heated to 45 C. Dropwise addition of anhydrous HCl gas (4.0 g, 0.11 mole) dissolved in 2-propanol (50 g, 0.83 mole) to the solution is completed in an hour and held an additional 4 hours. The solvent is removed under vacuum and the resulting compound is dried to constant weight. The title compound is received (18.6 g) as a yellow glassy solid whose structure is consistent with HNMR.

EXAMPLE 60

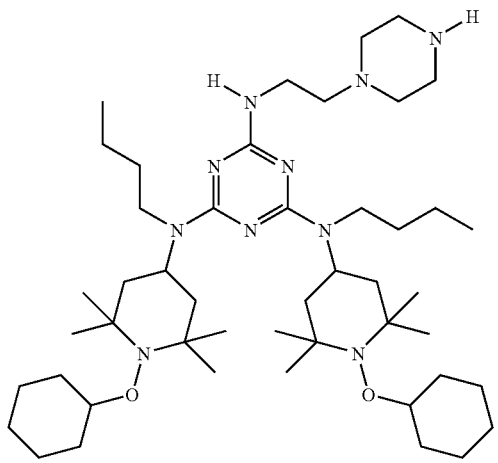

2,4-Bis[(1-cyclohexyloxy-2,2,6,6-tetramethylpiperidin-4-yl)butylamino]-6-chloro-1,3,5-triazine (40 g, 54.6 mmol) is mixed with N,N-dimethylformamide (220 g) and heated to 65° C. 1-(2-Aminoethyl)piperazine (14.5 g, 112.2 mmol) is then added quickly and the reaction is stirred at 65° C. After 2 hrs, cyclohexane (150 g) and water (65 g) are added and the mixture stirred for 10 minutes. The layers are allowed to separate and removed from the reactor. The bottom aqueous phase is returned to the pot, heated to 55° C. and water (112 g) is added. The aqueous layer is then washed twice at 55° C. with cyclohexane (50 g/each). The cyclohexane layers are combined and washed four times with water (30 g/each) at 55° C. The cyclohexane layer is dried briefly over anhydrous $Na_2SO_4$ before removing the solvent under reduced pressure until a constant weight is received. The title compound is received (43.4 g) as a light yellow solid whose structure is consistent with HNMR.

EXAMPLE 61

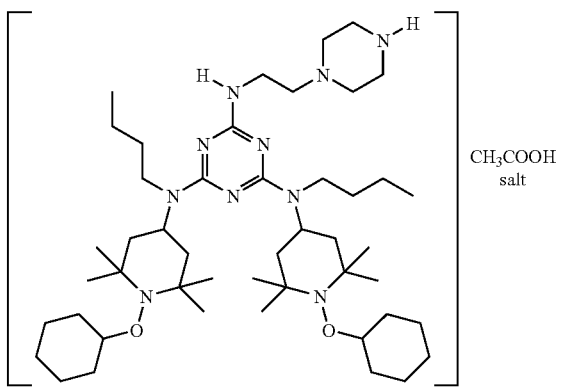

Example 60 is dissolved in 2-propanol. The product is then titrated with glacial acetic acid. The solvent is removed under vacuum and the resulting title compound is dried to constant weight.

EXAMPLE 62

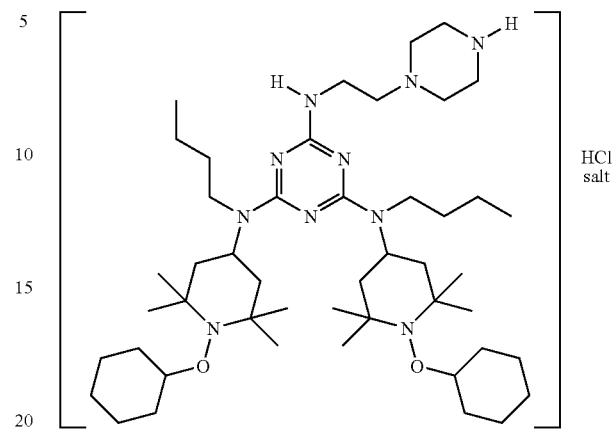

Example 60 (43.4 G, 53 mmol) is dissolved in cyclohexane (80 g). Anhydrous HCl Gas (2 g, 54.8 mmol) is dissolved in 2-propanol (12 g) and added to the cyclohexane solution. The mixture is stirred for 10 minutes and the solvent then distilled under reduced pressure to a constant weight. The title compound is obtained (45 g) as a light yellow solid whose structure is consistent with HNMR.

EXAMPLE 101

Formulation Reference: NeoResins, Inc., Formulation WB-2010, Technical Brochure, August, 2000

The following components are mixed together under good agitation:

| | |
|---|---|
| Butyl cellusolve | 5.68 parts |
| Carbitol | 4.26 parts |
| Triton X-100 | 0.25 parts |
| Water | 1.66 parts |
| Instant compound | 0.58 parts |

This solution is added to a 4 ounce clear glass jar containing 72.85 parts of NeoPac R-9699 under vigorous agitation and agitated for 10 minutes. Optionally, a defoamer, like Dehydran 1620 (Henkel), and a flash rusting agent, like Heiscore XAB (Cas Chem), are added. The lid is placed securely on the jar. The solidified coatings are visually observed for clarity after solidification. The development of opacity or haziness is indicative of an incompatibility between the hindered amine stabilizer and the formulated coating.

Solidified Coating in Jar

| Sample* | 0 days | 1 day | 19 days |
|---|---|---|---|
| A | clear | clear | clear |
| B | hazy | hazy | hazy |
| C | clear | clear | clear |
| D | clear | clear | clear |
| E | clear | clear | clear |
| F | clear | clear | clear |
| G | clear | clear | clear |
| H | clear | clear | clear |
| I | clear | clear | clear |
| J | clear | clear | clear |

-continued

| Sample* | 0 days | 1 day | 19 days |
|---------|--------|-------|---------|
| K | clear | clear | clear |
| L | clear | clear | clear |
| M | clear | clear | clear |
| N | clear | clear | clear |

*A is unstabilized. B contains 2% by weight of bis(1-octyloxy-2,2,6,6-tetramethylpiperidin-4-yl) sebacate. C contains 2% by weight of Instant Example 17. D contains 2% by weight of Instant Example 7. E contains 2% by weight of Instant Example 12. F contains 2% by weight of Instant Example 8. G contains 2% by weight of instant Example 57. H contains 2% by weight of Instant Example 59. I contains 2% by weight of Instant Example 53. J contains 2% by weight of Instant Example 62. K contains 2% by weight of Instant Example 111. L contains 2% by weight of Instant Example 107. M contains 2% by weight of Instant Example 105. N contains 2% by weight of Instant Example 109.

These data show that the instant compounds provide excellent solubility and compatibility in a high solids water borne urethane/acrylic copolymer coating system.

EXAMPLE 102

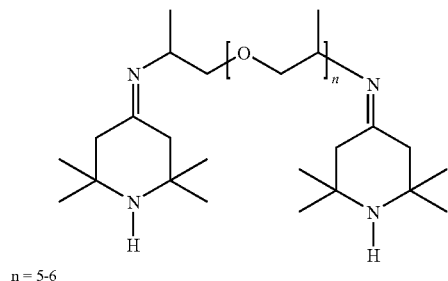

n = 5-6

2,2,6,6-Tetramethylpiperid-4-one (35 g, 0.2 mole) and Jeffamine D-400 (38.2 g, 0.095 mole, Huntsman) are added to cyclehexane (300 mL). The solution is heated to reflux and refluxed for four hours while collecting the water by-product in a Dean-Stark trap. Xylene (300 mL) is added and reflux is continued for four more hours. The solvent is removed by vacuum distillation and the resulting product is dried to constant weight. The title compound is received (69.2 g) as a viscous amber liquid whose structure is consistent with HNMR.

EXAMPLE 103

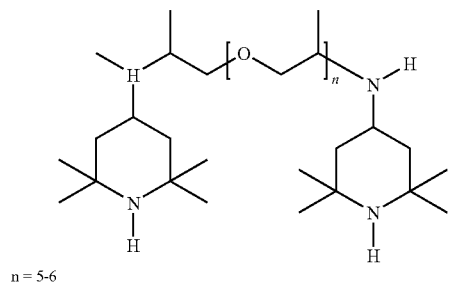

n = 5-6

Example 102 (30 g, 0.044 mole) is dissolved in ethanol (250 mL). Sodium borohydride (1.7 g, 0.044 mole) is added to the solution in one portion with agitation. The resulting solution is stirred overnight at ambient temperature. The solvent is removed by vacuum distillation and the residue is redissolved in ethyl acetate. The solution is washed repeatedly with water. The organic layer is then dried, the solvent removed by vacuum distillation, and the residue is dried to constant weight. The title compound is received (28 g) as a light yellow oil whose structure is consistent with HNMR.

EXAMPLE 104

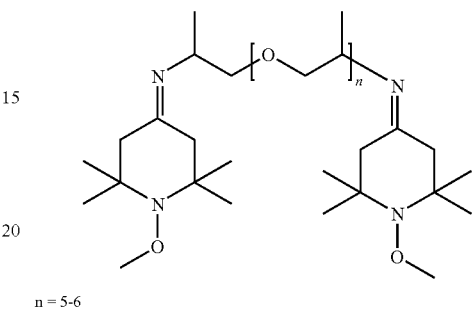

n = 5-6

1-Methoxy-2,2,6,6-tetramethylpiperid-4-one (20 g, 0.108 mole) and Jeffamine D-400 (22 g, 0.049 mole, Huntsman) are added to toluene (300 mL). The solution is heated to reflux and refluxed for four hours while collecting the water by-product in a Dean-Stark trap. The solvent is removed by vacuum distillation and the resulting product is dried to constant weight. The title compound is received (41 g) as a light yellow liquid whose structure is consistent with HNMR.

EXAMPLE 105

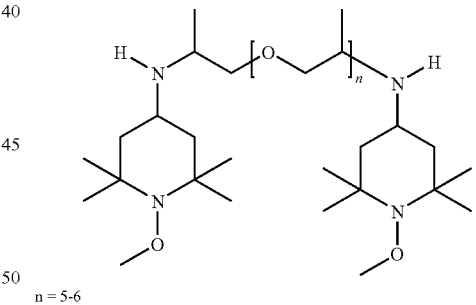

n = 5-6

Example 104 (30 g, 0.04 mole) is dissolved in ethanol (300 mL). Sodium borohydride (1.5 g, 0.04 mole) is added to the solution in one portion with agitation. The resulting solution is stirred overnight at ambient temperature. The solvent is removed by vacuum distillation and the residue is redissolved in ethyl acetate. The solution is washed repeatedly with water. The organic layer is then dried, the solvent removed by vacuum distillation, and the residue is dried to constant weight. The title compound is received (26 g) as a light yellow oil whose structure is consistent with HNMR.

This is an example of a compound of formula (7) where $R_5$ is a homooligomer of propylene oxide.

EXAMPLE 106

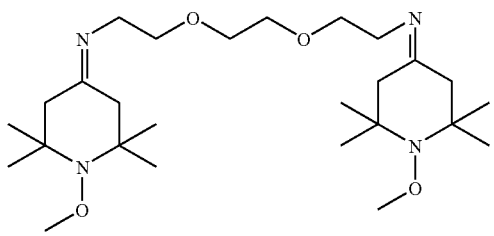

Following the procedure described in Example 104, 1-methoxy-2,2,6,6-tetramethylpiperid-4-one (25 g, 0.135 mole) and Jeffamine XTJ-504 (9.9 g, 0.067 mole, Huntsman) are reacted together. The title compound is received (32.4 g) as a light yellow oil whose structure is consistent with HNMR.

EXAMPLE 107

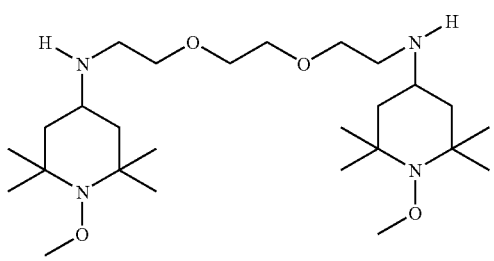

Following the synthetic procedure described in Example 105, Example 106 (32.4 g) is reduced to yield the title compound (26 g) as a light yellow oil whose structure is consistent with HNMR.

EXAMPLE 108

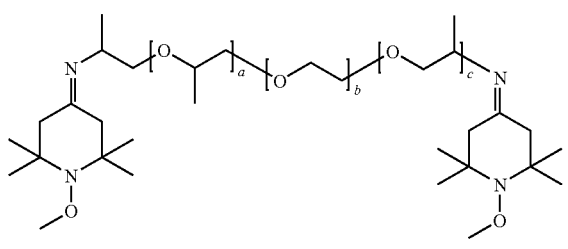

b = 9, a + c = 3.6

Following the procedure described in Example 104, 1-methoxy-2,2,6,6-tetramethylpiperid-4-one (6 g, 0.0324 mole) and Jeffamine XTJ-500 (10 g, 0.0166 mole, Huntsman) are reacted together. The title compound is received (15.4 g) as a light yellow oil whose structure is consistent with HNMR.

EXAMPLE 109

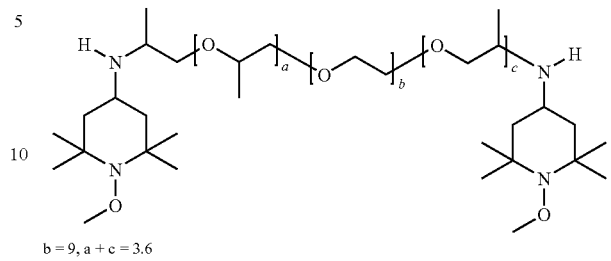

b = 9, a + c = 3.6

Following the synthetic procedure described in Example 105, Example 108 (15.4 g) is reduced to yield the title compound (14 g) as a light yellow oil whose structure is consistent with HNMR.

This compound is an example of a compound of formula (7) where $R_5$ is a co-oligomer of ethylene oxide and propylene oxide.

EXAMPLE 110

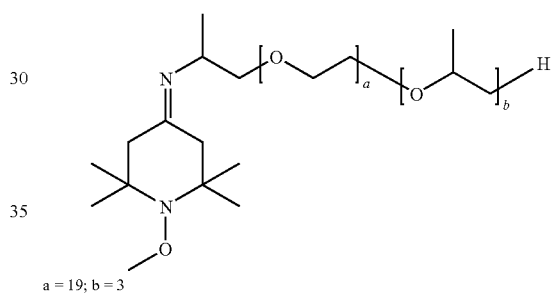

a = 19; b = 3

Following the procedure described in Example 104, 1-methoxy-2,2,6,6-tetramethylpiperid-4-one (25 g, 0.135 mole) and Jeffamine XTJ-506 (128 g, 0.128 mole, Huntsman) are reacted together. The title compound is received (150.5 g) as a light yellow oil whose structure is consistent with HNMR.

EXAMPLE 111

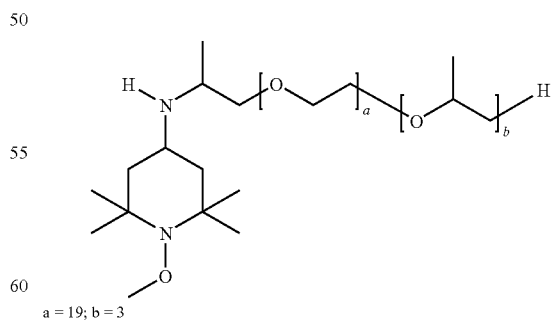

a = 19; b = 3

Following the synthetic procedure described in Example 105, Example 110 (150.5 g) is reduced to yield the title compound (44.1 g) as a light yellow oil whose structure is consistent with HNMR.

EXAMPLE 112

Formulation Reference: NeoResins, Inc., Formulation WB-2065, Technical Brochure

The following components are mixed together under good agitation:

| | |
|---|---|
| Water | 31.2 parts |
| Aqua Ammonia (26%) | 1.3 parts |

This solution is added to a 4 ounce clear glass jar containing 54.14 parts of NeoCryl BT-520 and 0.43 parts of Instant Stabilizer under vigorous agitation and is agitated for 10 minutes. The lid is placed securely on the jar. The liquid coating samples are visually observed for clarity over time. The development of opacity or haziness is indicative of an incompatibility between the hindered amine stabilizer and the formulated coating.

Liquid Coating in Jar

| Sample* | 0 | Day 1 | 1 Month |
|---|---|---|---|
| A | clear | clear | clear |
| B | hazy | hazy | hazy |
| C | clear | clear | clear |
| D | clear | clear | clear |
| E | clear | clear | clear |
| F | clear | clear | clear |

*A is unstabilized B contains 2% by weight of bis(1-octyloxy-2,2,6,6-tetramethylpiperidin-4-yl) sebacate C contains 2% by weight of Instant Example 111 D contains 2% by weight of Instant Example 107 E contains 2% by weight of Instant Example 105 F contains 2% by weight of Instant Example 109

These data show that the instant compounds provide excellent solubility and compatibility in an alkali-soluble, waterborne acrylic copolymer coating system.

EXAMPLE 113

Formulation Reference: Bayer Corp., 2K Waterborne Clear, Notebook #820894-A, Technical Brochure The following components are mixed together under good agitation:

| | | |
|---|---|---|
| Bayhydrol VP LS 2235 | 51.66 | parts |
| Deionized Water | 15.70 | parts |
| Borchigel LW 44 | 0.24 | parts |
| Instant Stabilizer | 1.15 | parts |
| UVA | 0.73 | parts |
| Baysilone Paint Additive VP AI 3468 | 0.28 | parts |

UVA is 2-(3-t-butyl-2-hydroxy-5-(2-(ω-hydroxy-octa-(ethyleneoxy)carbonyl-ethyl)-,phenyl)-2H-benzotriazole, a benzotriazole based UV absorber.

This solution is added to a 4 ounce clear glass jar containing 15.56 parts of Bayhydur XP-7165 and 3.91 parts of Exxate 700 under vigorous agitation and is agitated for 10 minutes. The lid is placed securely on the jar. The solidified coating samples are visually observed for clarity over time. The development of opacity or haziness is indicative of an incompatibility between the hindered amine stabilizer and the formulated coating.

Solidified Coating in Jar

| Sample* | 0 | Day 1 | 1 Month |
|---|---|---|---|
| A | clear | clear | clear |
| B | hazy | hazy | hazy |
| C | clear | clear | clear |
| D | clear | clear | clear |
| E | clear | clear | clear |
| F | clear | clear | clear |

*A is unstabilized B contains 2% by weight of bis(1-octyloxy-2,2,6,6-tetramethylpiperidin-4-yl) sebacate C contains 2% by weight of Instant Example 111 D contains 2% by weight of Instant Example 107 E contains 2% by weight of Instant Example 105 F contains 2% by weight of Instant Example 109

These data show that the instant compounds provide excellent solubility and compatibility in a two component, waterborne polyurethane coating system.

EXAMPLE 114

The hindered amine test stabilizers are incorporated into a coating system as described in Example 112. A 9.5-10 gram sample of each of the liquid coatings is added to a 100 mm×15 mm Petri dish and is placed in an oven at 65 C for thirty minutes. The samples are taken out of the oven, allowed to cool, and are visually observed for clarity over time. The development of opacity or haziness is indicative of an incompatibility between the hindered amine stabilizer and the formulated coating.

Solidified Coating in Petri Dish

| Sample* | 0 | Day 1 | 1 Month |
|---|---|---|---|
| A | clear | clear | clear |
| B | hazy | hazy | hazy |
| C | clear | clear | clear |
| D | clear | clear | clear |
| E | clear | clear | clear |
| F | clear | clear | clear |

*A is unstabilized B contains 2% by weight of bis(1-octyloxy-2,2,6,6-tetramethylpiperidin-4-yl) sebacate C contains 2% by weight of Instant Example 111 D contains 2% by weight of Instant Example 107 E contains 2% by weight of Instant Example 105 F contains 2% by weight of Instant Example 109

These data show that the instant compounds provide excellent solubility and compatibility in an alkali-soluble, waterborne acrylic copolymer coating system.

EXAMPLE 115

The hindered amine test stabilizers are incorporated into a coating system as described in Example 113. A 9.5-10 gram sample of each of the liquid coatings is added to a 100 mm×15 mm Petri dish and is placed in an oven at 75 C for 120 minutes. The samples are taken out of the oven, allowed to cool, and are visually observed for clarity over time. The development of opacity or haziness is indicative of an incompatibility between the hindered amine stabilizer and the formulated coating.

Solidified Coating in Petri Dish

| Sample* | 0 | Day 1 | 1 Month |
|---|---|---|---|
| A | clear | clear | clear |
| B | hazy | hazy | hazy |
| C | clear | clear | clear |

-continued

| Sample* | 0 | Day 1 | 1 Month |
|---------|-------|-------|---------|
| D | clear | clear | clear |
| E | clear | clear | clear |
| F | clear | clear | clear |

*A is unstabilized B contains 2% by weight of bis(1-octyloxy-2,2,6,6-tetramethylpiperidin-4-yl) sebacate C contains 2% by weight of Instant Example 111 D contains 2% by weight of Instant Example 107 E contains 2% by weight of Instant Example 105 F contains 2% by weight of Instant Example 109

These data show that the instant compounds provide excellent solubility and compatibility in a two component, waterborne polyurethane coating system.

What is claimed is:

1. A water compatible or water soluble sterically hindered hydroxy substituted alkoxyamine compound selected from the group consisting of compounds of formulae (5)-(7)

$$(5)$$

$$(6)$$

$$(7)$$

where
E is —O-T-(OH)$_b$,
T is a straight or branched chain alkylene of 1 to 18 carbon atoms, cycloalkylene of 5 to 18 carbon atoms, cycloalkenylene of 5 to 18 carbon atoms, a straight or branched chain alkylene of 1 to 4 carbon atoms substituted by phenyl or by phenyl substituted by one or two alkyl groups of 1 to 4 carbon atoms;
b is 1, 2 or 3 with the proviso that b cannot exceed the number of carbon atoms in T, and when b is 2 or 3, each hydroxyl group is attached to a different carbon atoms of T;
E' is hydrogen, $C_1$-$C_{18}$alkyl, $C_2$-$C_{18}$alkenyl, $C_7$-$C_{15}$phenylalkyl, $C_2$-$C_{18}$alkanoyl or phenyl, alkoxy of 1 to 18 carbon atoms, cycloalkoxy of 5 to 12 carbon atoms or aralkoxy of 7 to 15 carbon atoms, or E' is independently defined as for E,
R is hydrogen or methyl,
$R_5$ is a divalent homo- or co-oligomer consisting of monomer units derived from monomers selected from the group consisting of ethylene oxide, propylene oxide, ethylene glycol, propylene glycol, acrylic acid, methacrylic acid, ethylene imine, acrylamide, vinyl formamide, vinyl alcohol and vinyl acetate; which homo- or co-oligomer consists of between 2 and about 24 monomer units.

2. A compound according to claim 1 wherein T is a straight or branched chain alkylene of 1 to 12 carbon atoms, cycloalkylene of 5 to 12 carbon atoms, cycloalkenylene of 5 to 12 carbon atoms, or a straight or branched chain alkylene of 1 to 4 carbon atoms substituted by phenyl or by phenyl substituted by one or two alkyl groups of 1 to 4 carbon atoms.

3. A compound according to claim 1 where E is 2-hydroxy-cyclohexyloxy or 2-hydroxy-2-methylpropoxy.

4. A compound according to claim 1 of the formula $$(6)$$

$$(7)$$

5. A compound according to claim 1 where $R_5$ is polyethylene glycol or polypropylene glycol.

6. A stabilized composition comprising
an organic material subject to the deleterious effects of light, heat and oxygen, and
an effective stabilizing amount of a water compatible or water soluble sterically hindered alkoxyamine or hydroxy substituted alkoxyamine compound according to claim 1.

7. A composition according to claim 6 which is a coating, ink jet ink, ink jet recording material, photographic recording material, multi-layer polymer structure, a coextruded film, a radiation cured film, ink or coating; an adhesive or a laminate.

8. A composition according to claim 6 which additionally comprises an effective stabilizing amount of at least one coadditive stabilizer selected from the group consisting of the phenolic antioxidants, metal stearates, metal oxides, organophosphorus compounds, furanone antioxidants, hydroxylamines, ultraviolet light absorbers, and other hindered amine light stabilizers.

9. A composition according to claim 6 which additionally comprises an ultraviolet light absorber selected from the group consisting of the benzophenones, 2H-benzotriazoles and aryl-s-triazines.

10. A composition according to claim 6 which is a colored composition containing pigments or dyes.

11. A composition according to claim 6 which is a colored composition containing dyes.

12. A composition according to claim 6 which is a colored composition containing dyes, which composition is selected from the group consisting of ink jet inks, ink jet recording media, coatings, body care products, household products, textiles and fabrics.

13. A method for stabilizing ink-jet prints, which comprises applying to a recording material for ink-jet printing an ink composition containing a water soluble dye or a solution of a dye in an organic solvent and at least one compound of the formulae (5)-(7) as defined in claim 1 and drying said recording material.

14. A method for stabilizing ink-jet prints, which comprises applying to a recording material for ink-jet printing a casting or coating dispersion or an aqueous or organic solution containing at least one compound of the formulae (5)-(7) as defined in claim 1 and further applying either an ink composition containing a water soluble dye or a solution of a dye in an organic solvent; or an ink composition containing a water soluble dye or a solution of a dye in an organic solvent and at least one compound of the formulae (5)-(7) and drying said recording material.

* * * * *